(12) United States Patent
Harada et al.

(10) Patent No.: US 8,946,628 B2
(45) Date of Patent: Feb. 3, 2015

(54) ELECTRON BEAM INTERFERENCE DEVICE AND ELECTRON BEAM INTERFEROMETRY

(75) Inventors: Ken Harada, Fuchu (JP); Hiroto Kasai, Higashimatsuyama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/810,934

(22) PCT Filed: Feb. 3, 2012

(86) PCT No.: PCT/JP2012/000724
§ 371 (c)(1),
(2), (4) Date: Jan. 18, 2013

(87) PCT Pub. No.: WO2013/114464
PCT Pub. Date: Aug. 8, 2013

(65) Prior Publication Data
US 2014/0332684 A1 Nov. 13, 2014

(51) Int. Cl.
*G01N 23/00* (2006.01)
*G21K 7/00* (2006.01)
*H01J 37/252* (2006.01)
*G01N 23/04* (2006.01)
*H01J 37/26* (2006.01)
*H01J 37/147* (2006.01)

(52) U.S. Cl.
CPC .............. *H01J 37/252* (2013.01); *G01N 23/04* (2013.01); *H01J 37/26* (2013.01); *H01J 37/147* (2013.01); *H01J 2237/221* (2013.01); *H01J 2237/2505* (2013.01)
USPC ........... 250/307; 250/306; 250/309; 250/310; 250/311; 356/28.5

(58) Field of Classification Search
USPC .......... 250/306, 307, 309, 310, 311; 356/28.5
See application file for complete search history.

(56) References Cited

U.S. PATENT DOCUMENTS 7,538,323 B2 * 5/2009 Harada et al. ................. 250/310
2007/0272861 A1 11/2007 Harada et al.
2009/0045339 A1 2/2009 Harada et al.

FOREIGN PATENT DOCUMENTS

JP 2005-197165 A 7/2005
JP 2006-318734 A 11/2006

OTHER PUBLICATIONS

Rafal E. Dunin-Borkowski et al., "Magnetic Microstructure of Magnetotactic Bacteria by Electron Holography", Science, Dec. 4, 1998, pp. 1868-1870, vol. 282.
Ken Harada et al., "Profile Structure of Magnetic Flux Lines in Type-II Superconductor from a Rectangular Electron Hologram", Journal of Electron Microscopy, 2003, pp. 369-373, vol. 52, No. 4.

* cited by examiner

*Primary Examiner* — Jack Berman
*Assistant Examiner* — Meenakshi Sahu
(74) *Attorney, Agent, or Firm* — Crowell & Moring LLP

(57) ABSTRACT

There is a limit in range and distance in which an electron beam can interfere and electron interference is implemented within a range of a coherence length. Therefore, interference images are consecutively recorded for each interference region width from an interference image of a reference wave and an observation region adjacent to the reference wave by considering that a phase distribution regenerated and observed by an interference microscopy is a differential between phase distributions of two waves used for interference and a differential image between phase distributions of a predetermined observation region and a predetermined reference wave is acquired by acquiring integrating phase distributions acquired by individually regenerating the interference images. This work enables a wide range of interference image which is more than a coherence length by arranging phase distribution images performed and acquired in the respective phase distributions in a predetermined order.

14 Claims, 15 Drawing Sheets

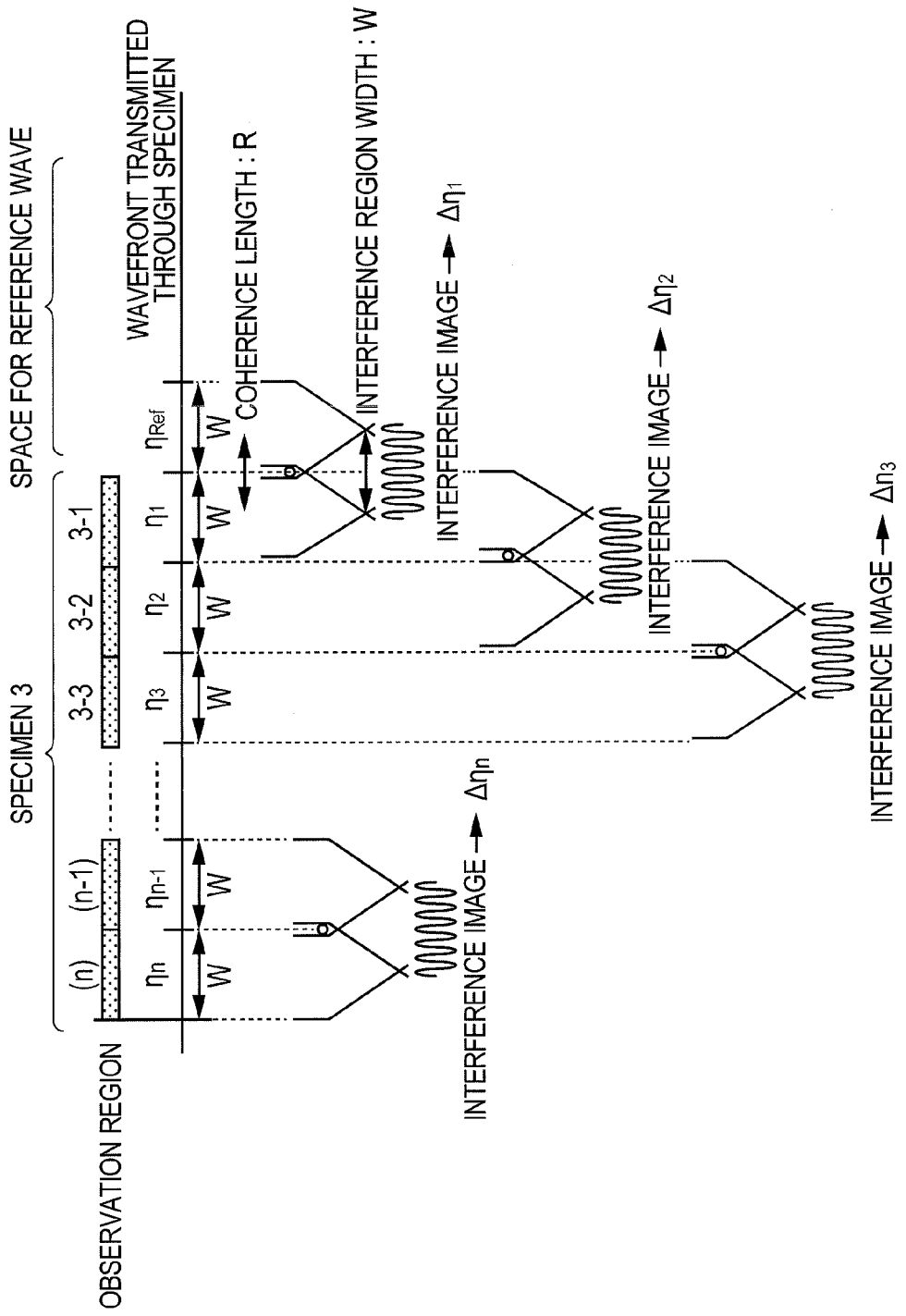

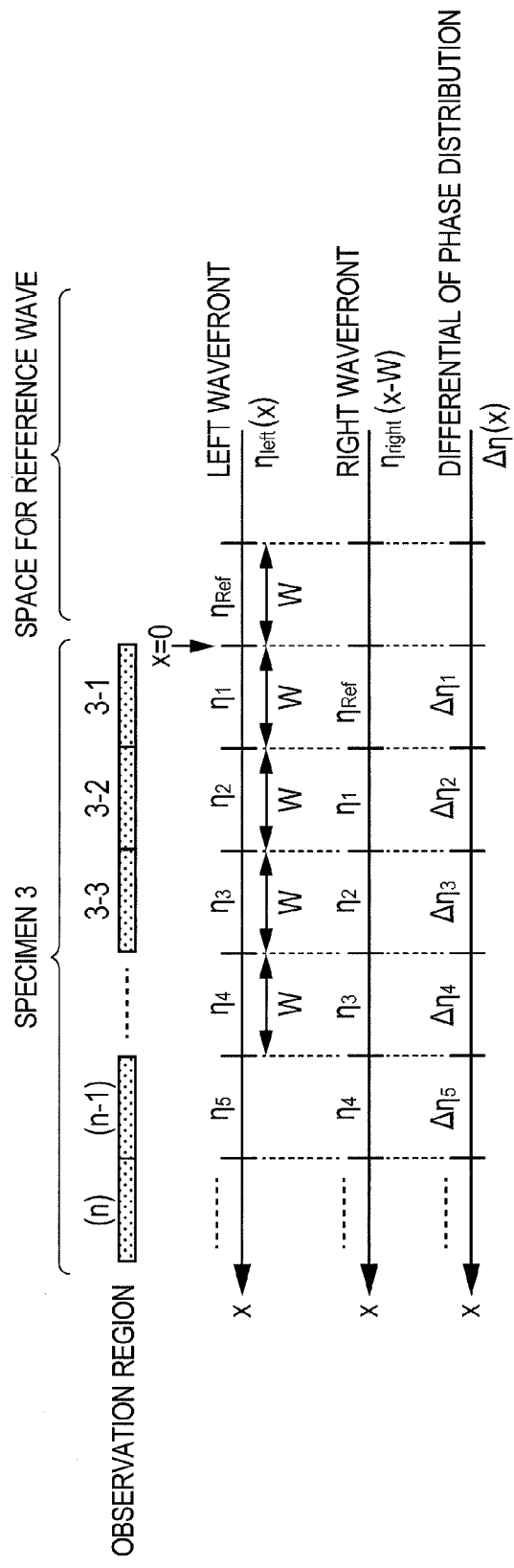

ELECTRON BEAM INTERFERENCE DEVICE AND ELECTRON BEAM INTERFEROMETRY

TECHNICAL FIELD

The present invention relates to an electron beam interference device and an electron beam interferometry that performs widespread interference measurement by using an electron beam.

BACKGROUND ART

Electron Biprism

An electron biprism as a device in an electron optical system that performs the same operation as a Fresnel biprism in optics includes two types of an electric field type and a magnetic field type. Therebetween, the electric field type electron biprism which has been widely spread has a shape illustrated in FIG. 10. That is, the electric field type electron biprism includes a filament electrode 9 at the center thereof and a parallel plate type ground electrode 99 maintained with the electrode interposed therebetween. For example, when constant voltage is applied to the central filament electrode 9, electron beams passing through a neighborhood of the central filament electrode 9 are deflected to face each other by potential of the central filament electrode as illustrated in FIG. 10 (see a trajectory 27 of the electron beam). A plane 25 is drawn vertically on the electron trajectory 27 in FIG. 10, and this is an equiphase surface when the electron beam is expressed as a wave and is generally called a wavefront as a surface vertical to the electron trajectory.

Potential that acts on the electron beam is decreased as the electronic beam is further spaced apart from the central filament electrode, but a space range on which the potential acts is lengthened, and as a result, a deflection angle of the electron beam does not depend on an incident position but is in proportion to voltage applied to the filament electrode. That is, when $\alpha$ is the deflection angle of the electron beam by the electron biprism, a simple relationship expressed as $\alpha=kVf$ by using the applied voltage $Vf$ to the central filament electrode and a deflection factor k is established. A primary feature of an electron optical device is that the deflection angle $\alpha$ of the electron beam does not depend on the incident position, and only a propagation direction of a plane wave is deflected as a state of the plane wave to inject the electron biprism. In that this corresponds to an effect of a biprism after two prisms are accurately matched in the optics, this is called an electron biprism.

The electron biprism using the potential is called the electric field type electron biprism and the electron biprism using Lorentz force of an electric field and the electron beam is called the magnetic field type electron biprism, in order to deflect the electron beam. In this application, the electric field type electron biprism will be used and described. However, in the present invention, as long as the electron biprism is a device in which the electron beams interfere with each other, the present invention may be configured regardless of the electric field type or the magnetic field type and the present invention is not limited to the electric field type electron biprism used in description. Further, when the 'electron biprism' is described in the specification of the present application (however, the claims are excluded), the electron biprism means the entirety of the electron biprism as an electron beam deflection device, which includes the central filament electrode in a wide sense, and when an exact position in the electron optical system is mentioned, principally the 'central filament electrode of the electron biprism' is described.

The electron biprism is a device required to make electron beam interference in an electron beam without a beam splitter such as a half mirror in the optics. The reason is a function of separating a wavefront 25 of one electron beam into two waves and deflecting two waves to face each other. As a result, the electron beam separated into two waves by passing through the electron biprism is overlapped in the rear of the electron biprism to generate an interference pattern 8. Such an electron optical system is collectively called an electron beam interference optical system.

Creation of Interference Microscope Image

The most general electron interferometer represented as electron holography is a one-stage electron biprism interferometer in which a single electron biprism (9 and 99) is interposed between an objective lens 5 and an image plane 71 of the specimen 3 by the objective lens, as illustrated in FIG. 11. In the single electron biprism interferometer, an electron beam (an objective wave 21, an electron beam passing through a right side of the central filament electrode 9 in FIG. 11) transmitted through the specimen 3 and an electron beam (a reference wave 23, an electron beam passing through a left side of the central filament electrode 9 in FIG. 11) transmitted through a part without the specimen superimpose on each other by applying plus voltage to the central filament electrode 9 to acquire an interference microscope image (31 and 8: an image in which the interference pattern 8 superimposes on a specimen image 31). A superimposition range of the object wave 21 and the reference wave 23 is the interference microscope image and is formed with a width W on the image plane 71 of the specimen 3 in the rear of the central filament electrode 9. This is called a width of an interference region.

That is, a phase change to which the specimen 3 gives onto the wavefront of the object wave 21 is recorded as modulation of the superimposed interference pattern 8. In the single electron biprism interferometer, Fresnel patterns by a diffraction wave generated from ends of the left and right filament electrodes 9 in the interference microscope image are included. Since this generally has a strong contrast and both the Fresnel patterns of a broad pattern interval and the Fresnel patterns of a small pattern interval are distributed in a wide range of spatial frequency band, the Fresnel patterns cause an artifact which is the largest problem as the interference microscope image 31 and 8. As a result, it is preferable that the Fresnel patterns are removed in image processing of extracting phase information of the interference image or the Fresnel patterns are prevented from being generated by contrivance in the electron optical system.

As a result, the contrived interferometer is a double electron biprism interferometer (Patent Document 1) and configures an optical system which can substantially arbitrarily control the interference region width W and the interference pattern interval as well as generation of the Fresnel patterns by using two electron biprisms. Unless particularly limited, in this application, a single electron biprism interference optical system illustrated in FIG. 11 is used and described for simplification, but the present invention is not limited to the single electron biprism interferometer.

Coherence Length

Wave motions of electrons which are Fermi particles are different from wave motions of photons which are Bose particles and cannot be degenerated as a state of one particle. Therefore, the wave motions of the electrons cannot be completely in a coherent state like a laser in a strict sense, and an energy distribution width is decreased by increasing stability in acceleration voltage and an angle distribution (an opening angle of the electron beam: β) of the motions of the electrons is decreased by decreasing the size of a light source as possible to contrive to extend a wavefront as an electron wave (a wavelength: λ). A range in which the electron wave can interfere is represented by a coherence length R and expressed by Equation 1. This length depends on the electron optical system, but in a magnetic field observation optical system, this length has a general value of approximately 1 μm on a plane of the specimen.

$$R = \lambda/2\beta \quad \text{[Equation 1]}$$

One example of the optical system of the electron holography representing an electron interference measurement method is illustrated in FIG. 11, but a relationship of Equation 2 is generally established between the coherence length R on the specimen plane (a plane of the object) and the interference region width W of hologram on the image 71 by considering a magnification ($Mo_{bj}=b/a$) by the objective lens 5 (both a and b are described in the figure). However, the thickness of the central filament electrode 9 of the electron biprism is disregarded for simplification. That is, existence of the central filament electrode 9 narrows the interference region width W.

$$W \leq b/a R \quad \text{[Equation 2]}$$

For example, when the interference region width W of FIG. 11 is approximately (b/a)R which is the coherence length after considering the magnification by the objective lens 5, interference with a region (ref: a spatial region with no specimen) of a reference wave and holography can be observed in an observation region 3-1 of the specimen, but a region (an observation region 3-2 to an observation region 3-5) further distant from an optical axis 2 than the observation region 3-1, that is, the inside of the specimen is out of the range of the coherence length and holography cannot be observed therein.

Two-Wave Interference

Interference of two wave fields φA and φB which are within the range of the coherence length will be described. Strictly, partial coherent handling is required, but full coherence is handled for display for convenience. When amplitude distributions are respectively set as φA(x, y) and φB(x, y) and phase distributions are respectively set as ηA(x, y) and ηB(x, y), an intensity distribution I(x, y) which waves expressed by Equations 3 and 4 create by interference is expressed by Equations 5 and 6.

$$\Phi_A(x,y) = \phi_A(x,y)\exp[i\eta_A(x,y)] \quad \text{[Equation 3]}$$

$$\Phi_B(x,y) = \phi_B(x,y)\exp[i\eta_B(x,y)] \quad \text{[Equation 4]}$$

[Equation 5]

$$I(x, y) = |\phi_A(x, y)|^2 + |\phi_B(x, y)|^2 + \frac{1}{2}\phi_A(x, y)\phi_B(x, y)\cos[(\eta_A(x, y) - \eta_B(x, y))] = |\phi_A|^2 + |\phi_B|^2 + \frac{1}{2}\phi_A\phi_B\cos[\Delta\eta(x, y)]$$

$$\Delta\eta(x,y) = \eta_A(x,y) - \eta_B(x,y) \quad \text{[Equation 6]}$$

A cosine term of a third term in Equation 5 is a term to form an interference pattern, which is related to the phase distribution of the wave motion. That is, in interference, a differential Δη(x, y) between the phase distributions of two wave motions is observed as the interference pattern. This indicates that although the phase distributions are regenerated by the interference measurement method, not the phase distributions of the respective wave motions but only the differential between the phase distributions is observed.

Electron Holography

The electron holography is also generally a measurement method by two-wave interference, and is characterized in that one of the two waves is an object wave $\phi_{Obj}$(x, y)exp [i$\eta_{Obj}$(x, y)] and the other one is a reference wave exp [iηRef(x, y)] which has already been known, such as a plane wave, and the like. That is, the holography is generally a method of measuring the object wave based on the reference wave which has already been known. In the case of the electron holography, since interference is made by using the electron biprism as illustrated in FIG. 10, the reference wave may be regarded as the plane wave which is inclined to the optical axis. For simplification, when the object wave propagates in parallel to the optical axis and only the reference wave propagates to be inclined in an X-axis direction at an angle α, the interference intensity distributions as the object wave, the reference wave, and the hologram (the interference microscope image) are expressed by Equations 7, 8, and 9 below. Further, $R_0$x in Equation 8 is a carrier spatial frequency.

$$\Phi_{Obj}(x,y) = \phi_{Obj}(x,y)\exp[i\eta_{Obj}(x,y)] \quad \text{[Equation 7]}$$

$$\Phi_{Ref}(x,y) = \exp[2\pi i R_{0x} x] \; (R_{0x} = \sin \alpha/\lambda \quad \text{[Equation 8]}$$

$$I_{Holo}(x,y) = |\phi_{Obj}(x,y)|^2 + 1 + \frac{1}{2}\phi_{Obj}(x,y))\cos[\eta_{Obj}(x,y) - 2\pi R_{0x} x] \quad \text{[Equation 9]}$$

In Equation 9, a hologram indicates that interference patterns of an interval of $1/R_0 x$, which is modulated by a phase distribution $\eta_{Obj}$(x, y) of a wave transmitted through an object in an image |$\phi_{Obj}$(x, y)|2 of the object are superimposed on each other, and the interference pattern distribution features the electron holography.

Although omitted herein, the amplitude distribution $\phi_{Obj}$(x, y) and the phase distribution $\eta_{Obj}$(x, y) of the object wave can be individually regenerated by image processing using a numerical operation such as a Fourier transformation method, and the like. However, as described above, as a differential in phase distribution between the phase distribution $\eta_{Obj}$(x, y) of the object wave and a phase distribution (Const, an integer number) of the plane wave, Δη(x, y)=$\eta_{Obj}$(x, y)−Const is acquired and as an offset of the phase distribution, the phase distribution $\eta_{Obj}$(x, y) of the object wave is acquired by considering Const (in this case, as zero).

Further, a method of connecting the respective regions regenerated by splitting the observation region to each other afterwards through image processing is used (Non-Patent Document 1). Even in this case, an observable region is within a range in which the reference wave is acquired and is just a neighboring part of the specimen.

CITATION LIST

Patent Literature

Patent Literature 1: Japanese Unexamined Patent Application Publication No. 2005-197165
Patent Literature 2: Japanese Unexamined Patent Application Publication No. 2006-318734

Non-Patent Literature

Non-Patent Literature 1: R. E. Dunin-Borkowski et al., Science 282, (1998) 1868.

Non-Patent Literature 2: K. Harada et al., J. Electron Microsc. 54, (2003) 369.

SUMMARY OF INVENTION

Technical Problem

In the related art, in order to implement the electron beam interferometry represented as the electron holography, a means of (1) increasing luminance of an electron source and creating an electron wave which has a sufficiently large coherence length with respect to an observation target or (2) contriving a specimen shape to secure a region of the reference wave at an appropriate position with respect to the observation target is adopted.

Development of a high-luminance electron source for (1) is basic and development of a field emission type electron gun for a transmissive electron microscope is used for this purpose. However, as described above, it is principal that the electrons are the Fermi particles and the electrons cannot be on part with the laser in terms of a coherence degree. Further, the luminance of the electron source determines basic performance of the electron microscope and is hardly changed after development of the electron microscope. As a result, the luminance is performance which depends on the device, and a range of a coherence length directly deduced from the luminance which can be contrived by the optical system is significantly limitative.

Further, as a realistic method, a contrivance of acquiring a hologram of which an SN ratio deteriorates by extending the observation region almost up to a coherence region with recent development of digital image processing and extracting only information required during regeneration or in image processing after the regeneration is made. However, when the observation region is over the coherence length, interference measurement is principally impossible. Alternatively, a method of connecting the respective regions regenerated by splitting the observation region to each other afterwards through image processing is used (Non-Patent Document 1). Even in this case, the observable region is also limited to the range in which the reference wave is acquired and thus is just the neighboring part of the specimen.

A space for the reference wave can be created by focusing on a neighboring of the observation target by using a specimen preparation method for the transmissive electron microscope by a focused ion beam (FIB) device. In holography observation of a semiconductor device, and the like, the specimen is almost prepared by the above method. However, a device (SiC device) having a size which is more than the coherence length or a specimen that extends in a broad range with a lamination structure cannot be actually prepared because the interference measurement has large restrictions.

As described above, a limitation problem of the size of the observable region in the electron beam interferometry is principal and a basic countermeasure is not actually present.

Solution to Problem

In order to solve the problem, an electron beam interference device of this application includes: a light source of an electron beam; an irradiation optical system for irradiating an electron beam emitted from the light source to a specimen; an imaging lens system having an objective lens that images an image of the specimen; an electron biprism disposed on an optical axis of the electron beam; an image recording device recording a plurality of phase distribution images in the specimen; and an image operation processing device operating the phase distribution images of the specimen, wherein the specimen includes a first observation region that an electron beam through which interferes with an electron beam transmitted through a reference wave region by the electron biprism is transmitted and a second observation region that an electron beam through which interferes with the electron beam transmitted through the first observation region by the electron biprism is transmitted, the image recording device records a second interference image based on the electron beam transmitted through the first observation region and the electron beam transmitted through the second observation region while recording a first interference image based on the electron beam transmitted through the reference wave region and the electron beam transmitted through the first observation region, and the image operation processing device operates phase distribution images of the electron beam transmitted through the reference wave region and the electron beam transmitted through the second observation region based on the second interference image recorded in the image recording device and the first interference image recorded in the image recording device.

Further, an electron beam interferometry of this application including a light source of an electron beam; an irradiation optical system for irradiating an electron beam emitted from the light source to a specimen; an imaging lens system having an objective lens that images an image of the specimen; an electron biprism disposed on an optical axis of the electron beam; an image recording device recording a plurality of interference images in the specimen; and an image operation processing device operating the phase distribution images of the specimen, includes: a first step of recording a first interference image based on a first observation region that an electron beam through which interferes with an electron beam transmitted through a reference wave region by the electron biprism is transmitted and the electron beam transmitted through the reference wave region; a second step of recording a second interference image based on a second observation region that an electron beam through which interferes with an electron beam transmitted through the second observation region by the electron biprism is transmitted, and the electron beam transmitted through the first observation region; and a third step of operating phase distribution images of the electron beam transmitted through the reference wave region and the electron beam transmitted through the second observation region based on the second interference image and the first interference image.

Further, an electron beam interferometry of this application including a light source of an electron beam; an irradiation optical system for irradiating an electron beam emitted from the light source to a specimen; an imaging lens system having an objective lens that images an image of the specimen; an electron biprism disposed on an optical axis of the electron beam; an image recording device recording a plurality of interference images in the specimen; and an image operation processing device operating the phase distribution images of the specimen, includes: a first step of recording a first interference image based on a first observation region that an electron beam through which interferes with an electron beam transmitted through a reference wave region by the electron biprism is transmitted and the electron beam transmitted through the reference wave region; a second step of recording a second interference image based on a second observation region that an electron beam through which interferes with an electron beam transmitted through the second observation region by the electron biprism is transmitted, and the electron beam transmitted through the first observation region; a third step of operating first phase distribution images of the electron beam transmitted through the reference wave region and the electron beam transmitted through the first observation region based on the first interference image; a fourth step of operating second phase distribution images of the electron beam transmitted through the first observation region and the electron beam transmitted through the second observation region based on the second interference image; and a fifth step of arranging and displaying the operated first and second phase distribution images in the order in which interference images which become origins of the operated phase distribution images are recorded.

Advantageous Effects of Invention

By applying the present invention, it is possible to holography-observe a wider range of specimens than the related art.

BRIEF DESCRIPTION OF DRAWINGS

FIG. 1 is a mimetic diagram describing a method of preparing interference images which are consecutive for each of adjacent regions.

FIG. 7(a) is a mimetic diagram illustrating a spatial positional relationship at the time of subtraction of phase distributions (wavefronts) when a projection width df of a central filament electrode is disregarded.

DESCRIPTION OF EMBODIMENTS

Figure 2A:
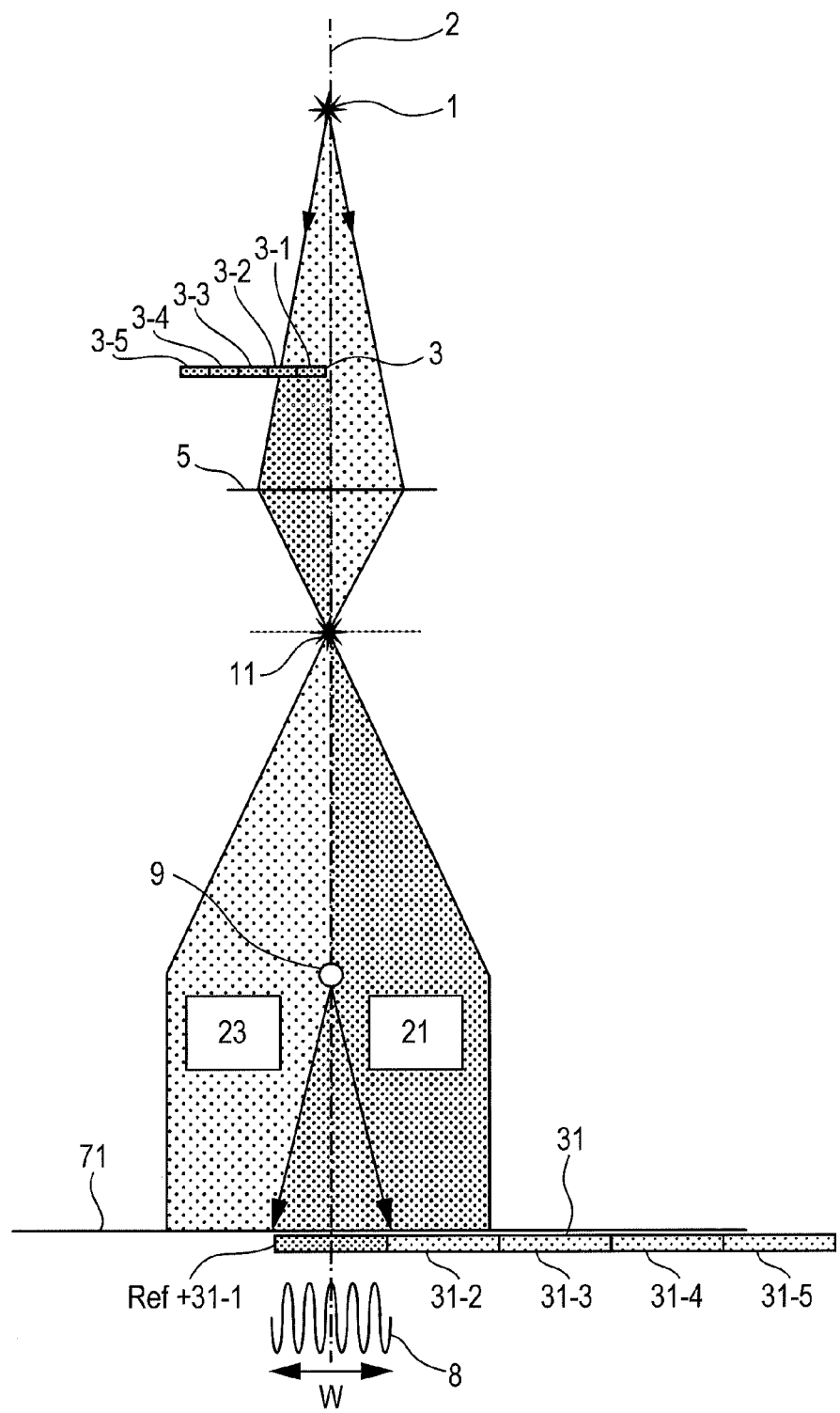
FIG. 2(a) is a mimetic diagram describing that consecutive interference images are prepared by moving a specimen.

The present inventor contrived a method of acquiring a differential image of a phase distribution between a predetermined observation region and a predetermined reference wave by recording interference images acquired by slightly moving a region for each interference region width from interference images between a reference wave region and an observation region adjacent to the reference wave and acquiring integration of phase distributions acquired by individually regenerating the interference images. This considers that a phase distribution regenerated and observed by an interference microscope method is a differential (see Equation 5) of respective phase distributions of two waves used in interference.

That is, the present invention is a method of observing the interference image between the predetermined observation region and the reference wave, that is, general holography by accumulating the respective phase distribution images after sequentially recording the interference images and regenerating the phase distribution images from the respective interference images while moving by an interference region width W recorded as the interference image (hologram) without distinguishing an object wave and the reference wave in a direction in which a coherence length is limited, and a device therefor.

In addition, according to the present invention, although a distance between a final observation region and the reference wave is more than the coherence length, when respective phase images are acquired, a phase distribution image using a predetermined reference wave is acquired even with respect to a phase distribution which is more than the coherence length. Further, this work is performed in the respective phase distributions and the acquired phase distribution images are arranged in a predetermined order to acquire a wide range of interference image which is more than the coherence length.

First Embodiment

First, the simplest case will be described by using FIGS. 1(a) and 1(b).

(1) An interference image (hologram) between a region Ref of the reference wave (phase distribution: $\eta \text{Ref}(x, y)$) and an observation region 3-1 (phase distribution: $\eta 1(x, y)$) in a specimen is recorded, and regenerated (operated and processed) by a holography technology. In this case, as a regeneration method, any method may be used and for example, the regeneration method may be for example, a Fourier conversion method or a phase shift method. The acquired regenerated phase distribution image is a differential $\Delta\eta 1(x, y)$ between phase distributions of two wave motions expressed by Equation 10.

$$\Delta\eta_1(x,y) = \eta_1(x,y) - \eta_{Ref}(x,y) \quad \text{[Equation 10]}$$

For example, when a plane wave is used as the reference wave, an influence of a phase of the reference wave is only an influence as an offset of the phase distribution of the observation region 3-1 as described above, and as a result, the phase distribution η1(x, y) of the observation region 3-1 may be acquired (Equation 11).

$$\eta_1(x,y) = \Delta\eta_1(x,y)$$ [Equation 11]

(2) Next, an interference image (hologram) between the observation region 3-1 (phase distribution: η1(x, y)) and an observation region 3-2 (phase distribution: η2(x, y)) in the specimen is recorded and regenerated by the holography technology. The acquired regenerated phase distribution image is a differential Δη2(x, y) between phase distributions of two wave motions expressed by Equation 12.

$$\Delta\eta_2(x,y) = \eta_2(x,y) - \eta_1(x,y)$$ [Equation 12]

(3) Next, an interference image (hologram) between the observation region 3-2 (phase distribution: η2(x, y)) and an observation region 3-3 (phase distribution: η3(x, y)) in the specimen is recorded and regenerated by the holography technology. The acquired regenerated phase distribution image is Δη3(x, y) (Equation 13). Further, the procedure is repeated similarly even with respect to next observation regions 3-4, and the like.

$$\Delta\eta_3(x,y) = \eta_3(x,y) - \eta_2(x,y)$$ [Equation 13]

(4) When the procedure is repeated even with respect to a predetermined observation region n (phase distribution, ηn(x, y)), the acquired regenerated phase distribution image is Δηn(x, y) (Equation 14).

$$\Delta\eta_n(x,y) = \eta_n(x,y) - \eta_{n-1}(x,y)$$ [Equation 14]

When the sum of phase distribution images from the observation region 3-1 to the observation region n is acquired, a subtraction term of each equation is offset, and as a result, only ηn(x, y) which is a phase distribution of the observation region n remains (Equation 15).
[Equation 15]

$$\sum_{k=1}^{n} \Delta\eta_k(x, y) = \eta_n(x, y) - \eta_{Ref}(x, y) = \eta_n(x, y)$$

It is apparent that this is a phase distribution regenerated from holograms of the observation region n and the region Ref of the reference wave (phase distribution: ηRef(x, y)). That is, the observation region n which is not in a neighboring part of the reference wave region Ref is regenerated by the interference image (hologram) using the reference wave region Ref.

(6) When the procedure (5) is repeated with respect to the observation regions n-1, n-2, . . . , 3-3, 3-2, and 3-1, all regions where the work is performed are regenerated as holograms using the same reference wave region Ref.

(7) When the respective phase distribution images acquired by the procedure (6) are enumerated and arranged in the order of these works, all the regions from the observation region 3-1 to the observation region n are widely observed as the phase distribution images. That is, wide-field holography which does not depend on the coherence length is implemented. Further, all of the acquired images are not arranged, but only a phase distribution image corresponding to an observation region which is desired to be observed may also naturally be generated.

(8) In addition, examples of the method of sequentially moving a region of an interference image where observation and recording are performed include three methods of (i) moving the specimen, (ii) moving an electron biprism, and (iii) making a propagation angle of an electron beam be inclined. The respective methods have features, but the most convenient and effective method is the method of (i) moving the specimen.

In this method, it is based on the premise that the phase distributions of the respective observation regions n-1, . . . , 3-3, 3-2, and 3-1 from the observation region n to the reference wave region Ref are offset as described in Equation 15. To this end, spatial positions of the respective phase distributions which are offset need to coincide with each other. As a result, as necessary, a work of adjusting the positions of the respective phase distribution images or adjusting the positional relationships of the respective images in observation and recording is included.

Further, in order to make the adjustment work most convenient, it is reasonable that a movement direction of the observation region is a length direction and a vertical direction of a projection image onto a specimen of a central filament electrode of the electron biprism observed in a strip shape or a line shape. However, this application is not limited to the movement direction. Hereinafter, an interference microscope device and a method which are suitable for implementing the present invention will be described.

Second Embodiment

Figure 2B:
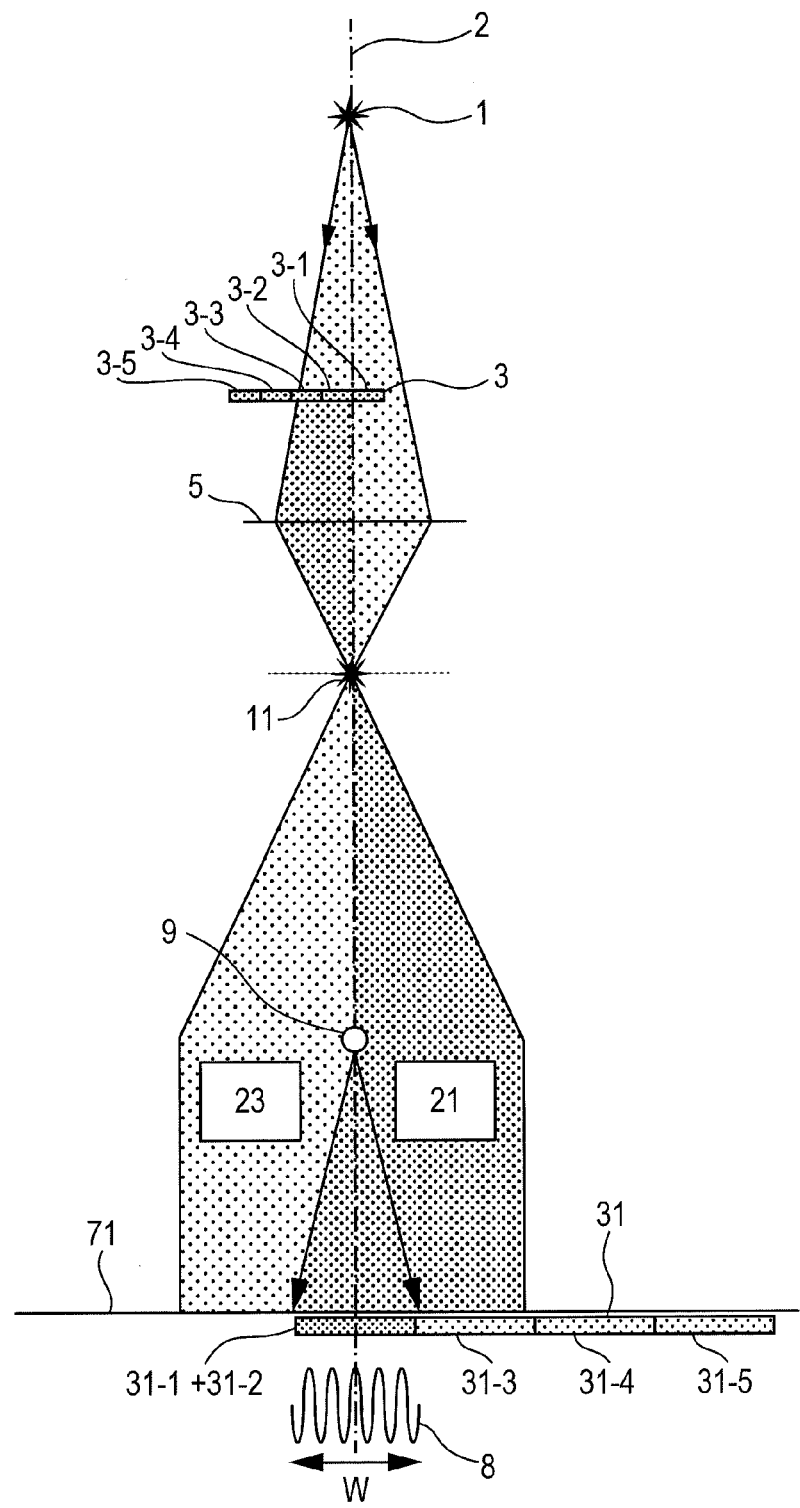
FIG. 2(b) is a mimetic diagram describing that consecutive interference images are prepared by moving the specimen to a right side further than FIG. 2(a).

FIGS. 2(*a*) and 2(*b*) illustrate an optical system device and a method that slightly moves regions of interference images 8+31 by sequentially moving the specimen 3. FIG. 2(*a*) illustrates that the interference images 8+31 by the reference wave region Ref and the observation region 3-1 are prepared, and illustrates a state of an optical system at the time of observing electron interference (electron holography) which is generally made. Further, FIG. 2(*b*) illustrates a state of the optical system after moving the specimen 3 to a right side in the figure by an observation region width W. The interference images 8+31 by the observation region 3-1 and the observation region 3-2 is recorded on an image plane 71. It is characterized that in FIG. 2(*a*), a specimen region and a vacuum region are disposed with an optical axis 2 interposed therebetween, but in FIG. 2(*b*), the optical axis 2 is positioned in the specimen region. The interference image by the observation region 3-2 and the observation region 3-3 is recorded after recording the interference image in the state of FIG. 2(*b*) and by moving the specimen in this direction by the observation region width W. An observation region in a predetermined range is recorded as the interference image by sequentially repeating this work.

In general, since the specimen tends to be thicker as the specimen is further spaced apart from a boundary region (specimen edge) from vacuum, it becomes difficult to acquire an excellent contrast of an interference pattern in the interference image between the observation region and the observation region. However, this problem may be improved by the specimen preparation method using the focused ion beam (FIB) device. Further, development of an electron beam source having high transmittability in the specimen is also made while maintaining coherency of the electron beam, such as development an 1MV interference type electron microscope, and the like, and as a result, there is no principle problem in observation and recording of an interference image between the observation region and the other observation region. The thickness of the specimen will be described similarly even in subsequent embodiments and hereinafter, the description thereof will be omitted.

In the method described in the second embodiment, since the optical system is not manipulated during a series of interference image recording works, when optical conditions such as an interference region width, an interference pattern interval, an observation and recording magnification, and the like are first set, readjustment of the optical system is not required during the work. Further, since the magnification, and the like are recorded under the same condition, a wide range of phase distribution images may be acquired by performing image arrangement as it is after acquiring a regeneration image or integrating the phase distributions.

Figure 3A:
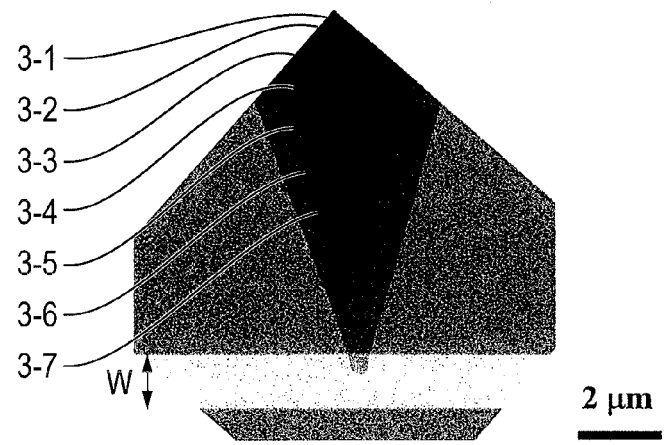
FIG. 3(a) is a diagram illustrating an experimental result in which the consecutive interference images are recorded by moving the specimen.

FIG. 3 illustrates an experimental example performed by the method illustrated in FIG. 2. In the specimen, a magnetic line distribution which leaks to a space from a neighboring part of a tip is observed with the tip of a magnetic force microscope (MFM). In FIG. 3(a), all images photographed while moving the specimen are stacked to one image and an interference region shown in a white strip shape is recorded while moving a specimen tip downward in the figure sequentially from a state of an upper side 3-1 to a state of 3-7 in the figure. For display convenience, a number indicating a region is given to the position of the tip and for example, a spatial region having the white strip shape is observed in the state of 3-1 and the case of the experimental example corresponds to the state where a space most spaced apart from the tip is observed. Since this state corresponds to observing a region most adjacent to the reference wave in FIG. 1, the same number 3-1 is given. Similarly even in another observation region, corresponding numbers from 3-1 to n of FIG. 1 are given. Further, n=7 in the case of FIG. 3, but n is not limited to the numerical value.

Figure 3B:
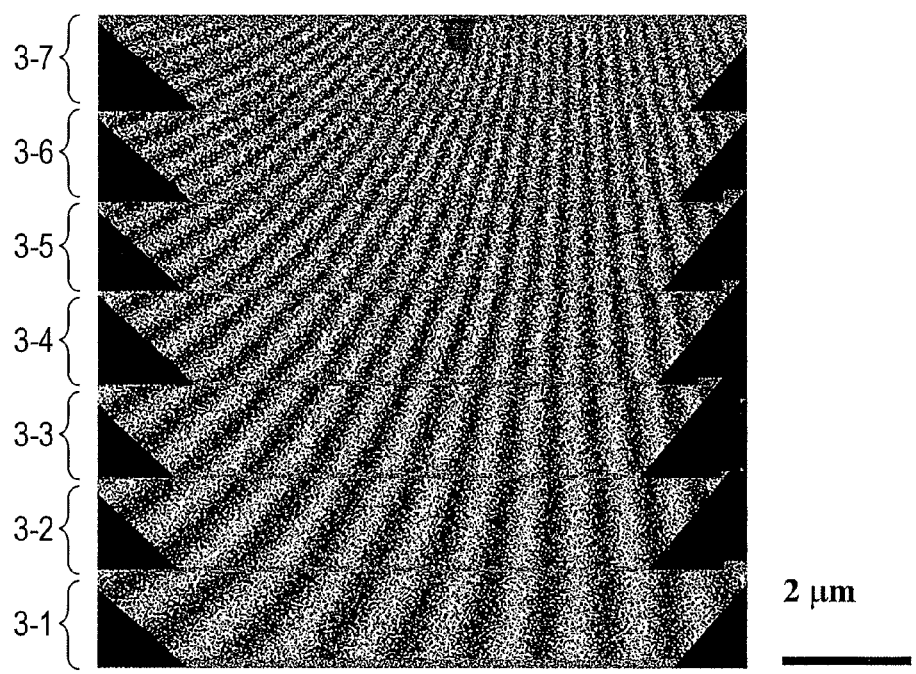
FIG. 3(b) is a wide range of magnetic line distribution image acquired by arranging phase distribution images regenerated from the consecutive interference images through predetermined integration processing.

In FIG. 3(b), after the regenerated phase distributions of the respective observation regions of FIG. 3(a) are acquired, the regenerated phase distributions are integrated as many as predetermined phase distributions and thereafter, a wide range of phase distribution image is formed according to a predetermined spatial position. It can be seen that as a magnetic line generated from the tip and a neighboring part thereof is spaced apart from the tip, the magnetic line is changed in a wide distribution. A number given in FIG. 3(b) is a number of the observation region. Further, in FIG. 3, a projection width of the central filament electrode of the electron biprism is displayed with an influence thereof disregarded. Handling the projection width of the central filament electrode will be described below.

In addition, in a series of experiments of FIG. 3, a double electron biprism interferometry (Patent Document 1) is used. In the double electron biprism interferometry, since the interference region width is strictly determined, the double electron biprism interferometry can be said to be more suitable for this method of consecutively recording the interference image by moving for each interference region. However, the procedure may also be implemented in a single electron biprism interferometry.

Third Embodiment

FIG. 4 illustrates an optical system device and a method that slightly move the region of the interference image 8+31 by sequentially moving the central filament electrode 9 of the electron biprism in a length direction (that is, an extension direction) and a vertical direction of a projection image of the electron biprism. Since the central filament electrode 9 of the electron biprism has a primary shape, there is no change in a length direction (that is, the extension direction) of a thin line. Therefore, a movement direction of the electron biprism need not particularly be vertical to the length direction of the thin line, and as a result, the electron biprism may be moved in the vertical direction to the length direction of the thin line.

Figure 4A:
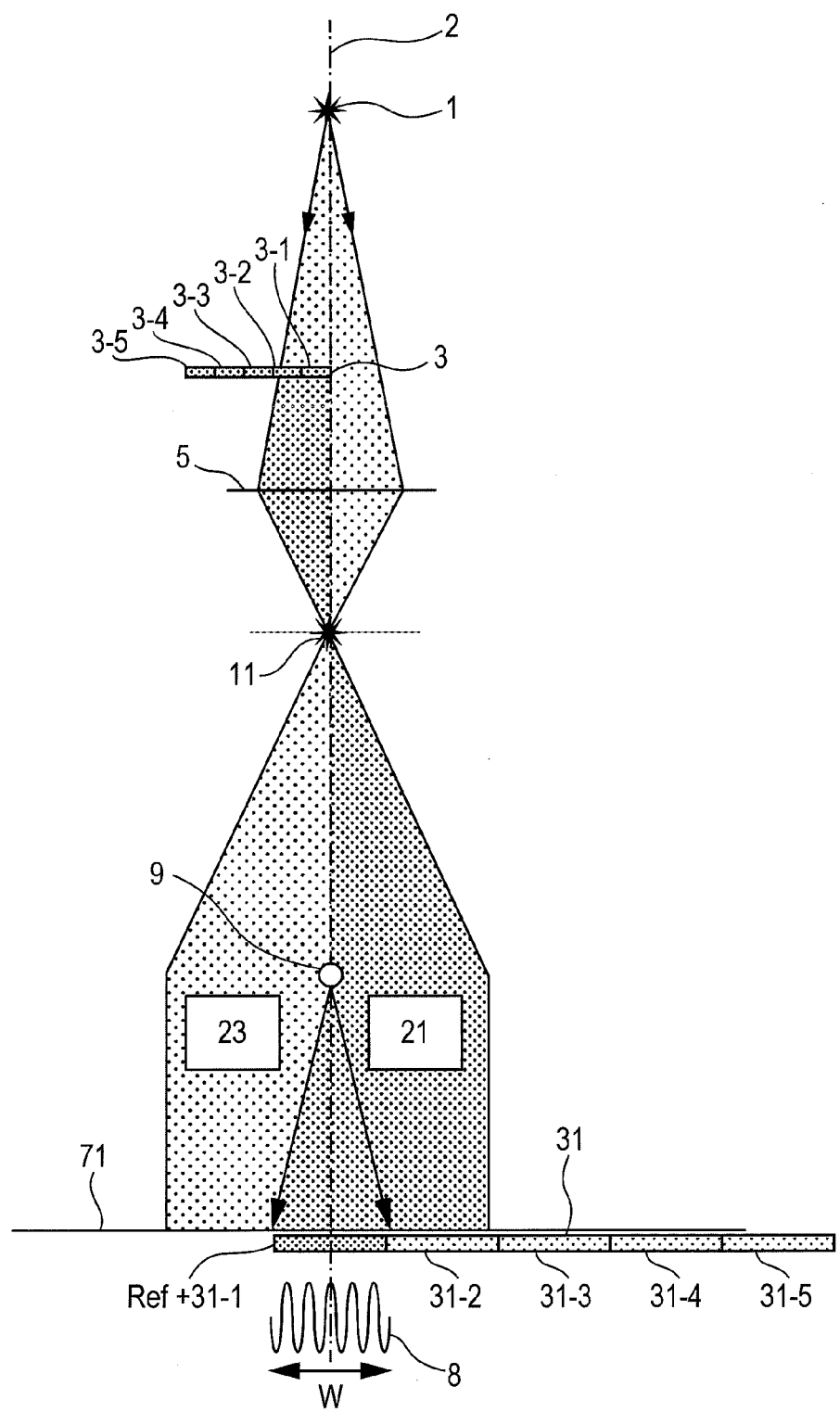
FIG. 4(a) is a mimetic diagram describing that consecutive interference images are prepared by moving an electron biprism.

FIG. 4(a) is the same as FIG. 2(a), and illustrates that the filament electrode 9 of the electron biprism is disposed on the optical axis 2, and the specimen region and the vacuum region are disposed with the optical axis 2 interposed therebetween, and as a result, the interference image 8+31 by the reference wave region Ref and the observation region 3-1 is prepared. That is, this is a state of the optical system at the time of observing general electron beam interference (electron holography).

Figure 4B:
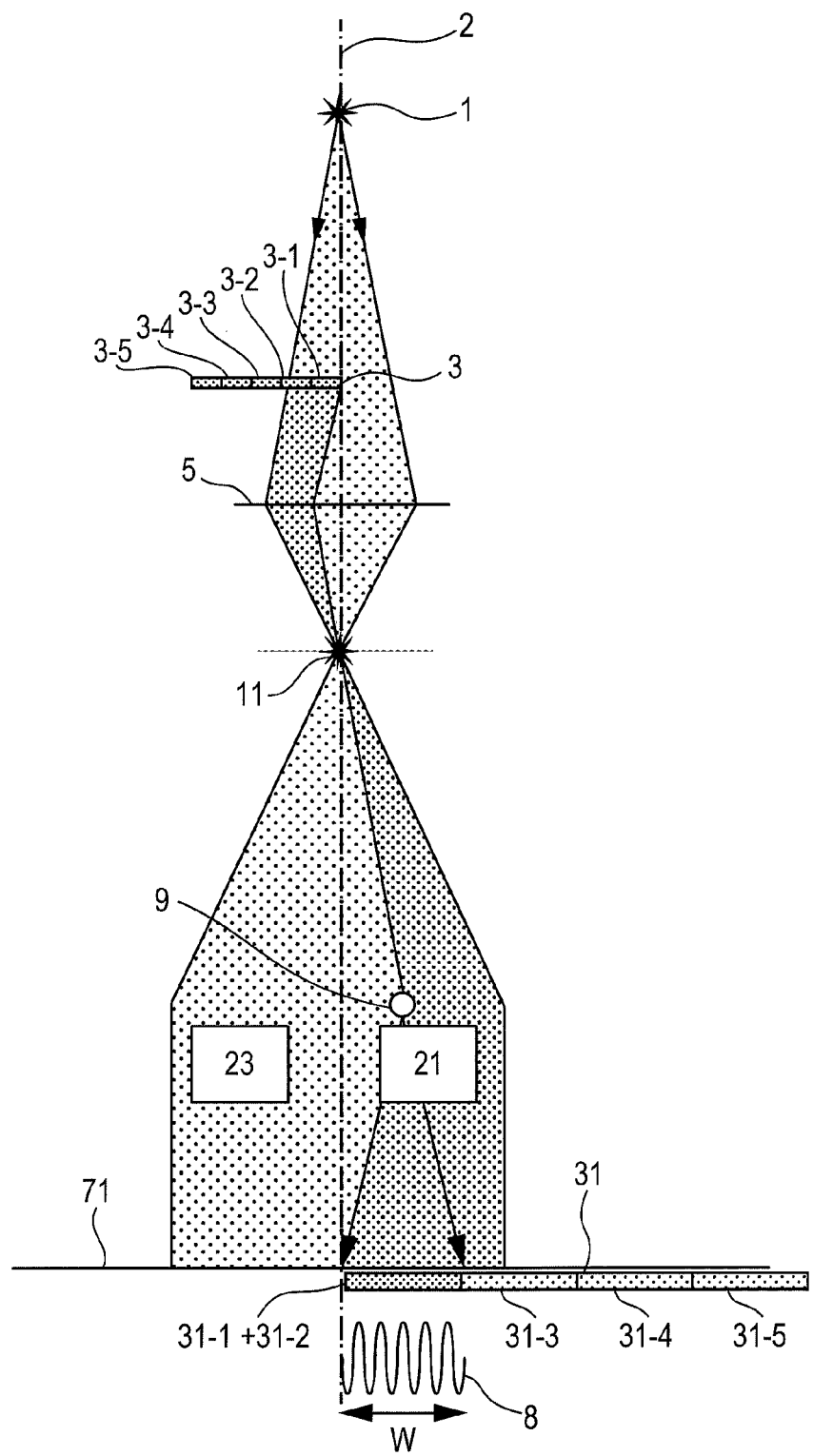
FIG. 4(b) is a mimetic diagram describing that consecutive interference images are prepared by moving the electron biprism to a right side further than FIG. 4(a).

FIG. 4(b) illustrates a state of the optical system after moving the central filament electrode 9 of the electron biprism to a right side in the figure. A movement amount of the central filament electrode 9 is an amount required for the interference image 8+31 by the observation region 3-1 and the observation region 3-2 to be recorded on the image plane 71, and the movement amount depends on the magnification of the optical system illustrated in FIG. 4 or the position (a height on the optical axis) of the central filament electrode 9 of the electron biprism in the optical system, and is generally approximately several microns and a sufficiently adjustable range. Similarly as the second embodiment, an observation region in a predetermined range is recorded as the interference image by sequentially repeating the work of recording the interference image by the observation region 3-2 and the observation region 3-3 after recording the interference image in the state of FIG. 4(b) and by moving the central filament electrode 9 of the electron biprism in this direction. With the movement of the central filament electrode 9 of the electron biprism, the position on the image plane 71 where the interference image is formed is also moved and the movement is not displayed in FIG. 4, but the movement is compensated by using an imaging lens system below an objective lens 5 and a deflection system in a magnifying lens system (see FIG. 6).

In the method described in the third embodiment, the movement amount of the electron biprism is generally larger than that of the specimen by the magnification of the optical system and precision in micromotion control of the electron biprism may be smaller than that in micromotion of the specimen. As a result, it is advantageous in improvement of resolution in this method. However, when the third embodiment is implemented by using the double electron biprism interferometer (Patent Document 1), two electron biprisms need to interlock with each other with a predetermined correlation. As a result, a complication of the work is increased, but this complication is not problematic in a system controlled by a computer (Patent Document 2).

Even in the method described in the third embodiment, since the optical system is not manipulated during a series of interference image recording works, when optical conditions such as an interference region width, an interference pattern interval, an observation and recording magnification, and the like are first set, readjustment of the optical system is not required during the work except for the aforementioned positional adjustment of the interference image on the image plane. According to the above configuration, since the magnification and the like are recorded under the same condition, a wide range of phase distribution images may be acquired by performing image arrangement as it is after operating a regeneration image or integrating the phase distributions.

Fourth Embodiment

Figure 5A:
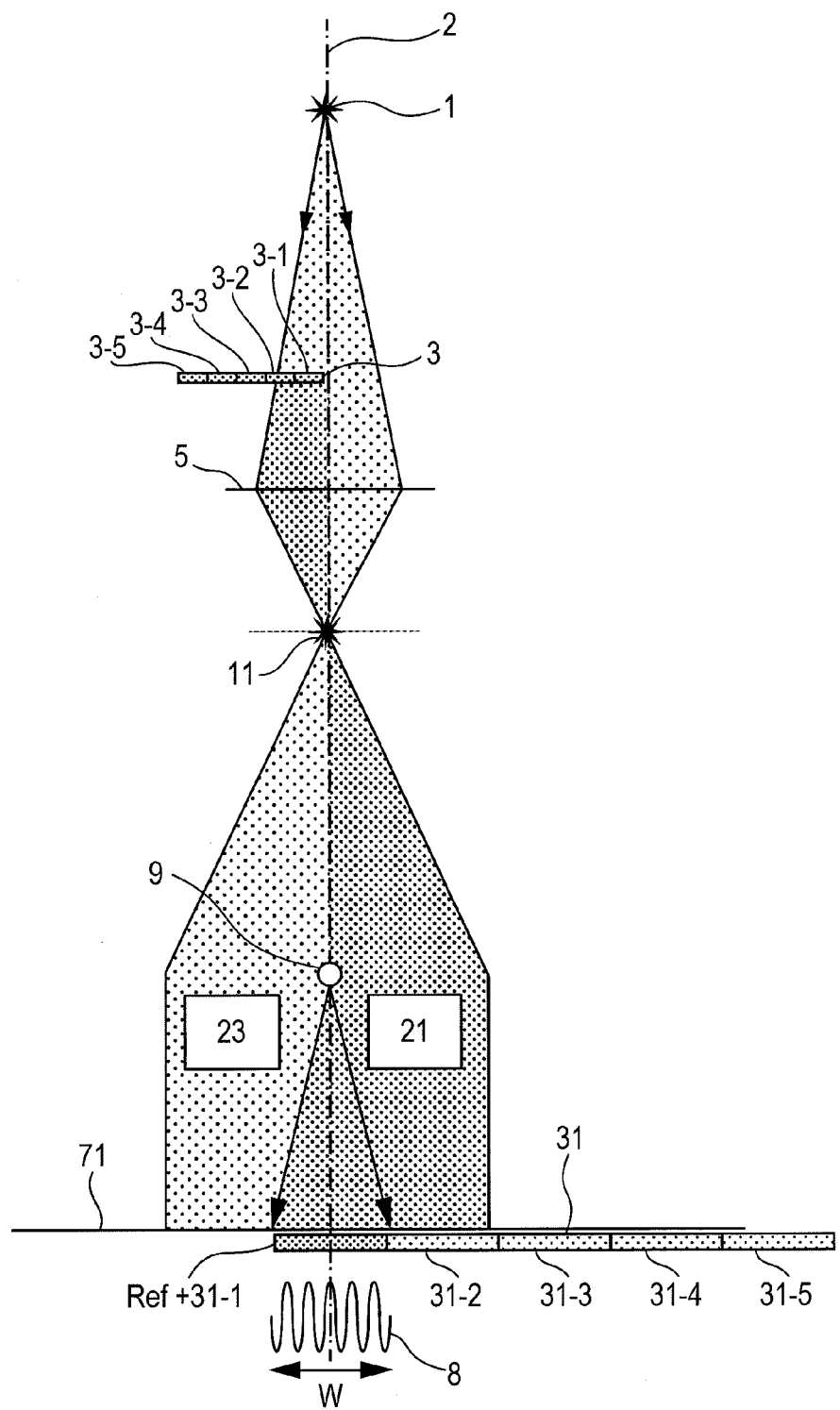
FIG. 5(a) is a mimetic diagram describing that consecutive interference images are prepared by deflecting an irradiation angle of an electron beam.
Figure 5B:
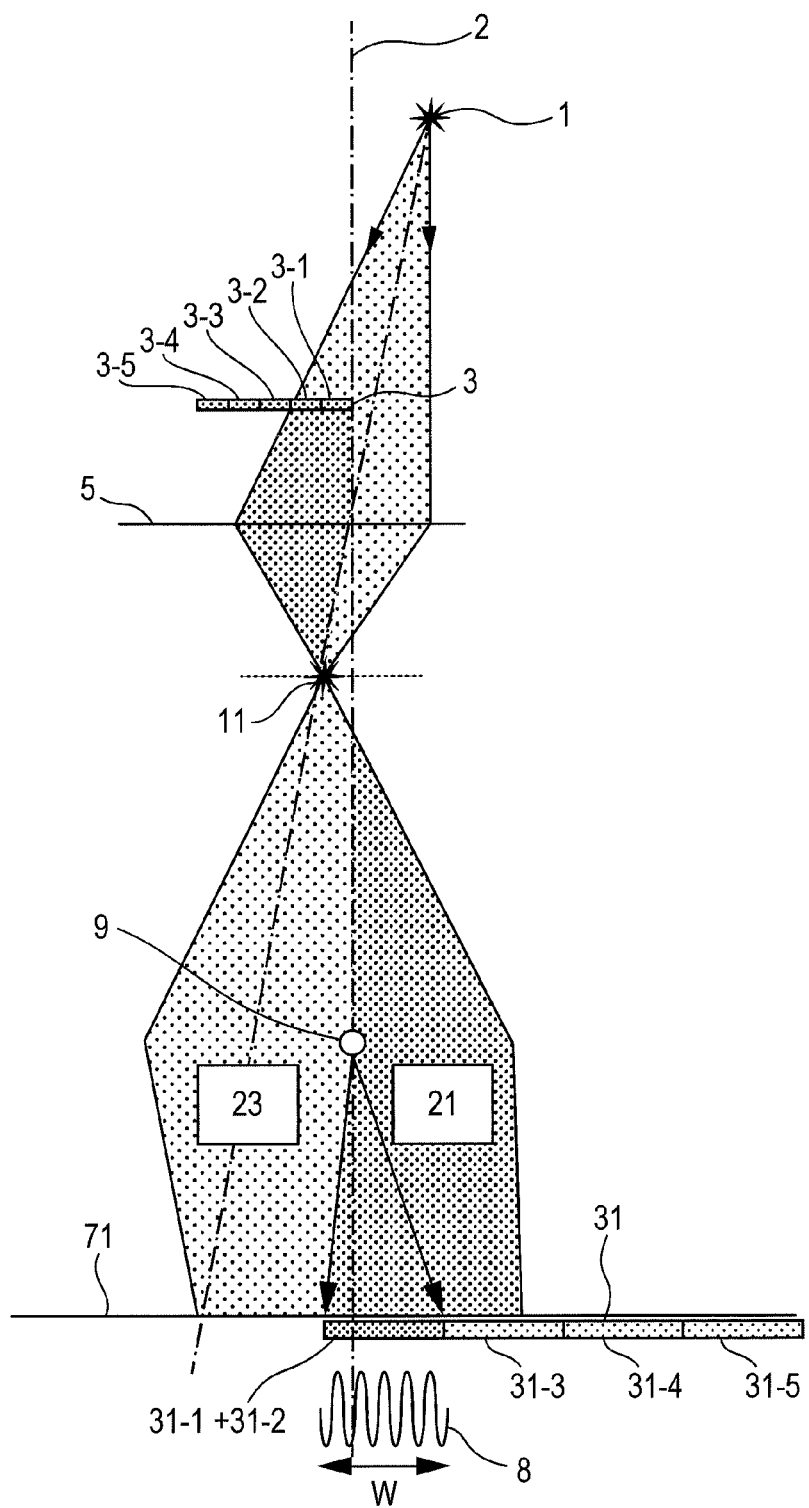
FIG. 5(b) is a mimetic diagram describing that consecutive interference images are prepared by deflecting an irradiation angle of the electron beam to a right side further than FIG. 5(a).

FIG. 5 illustrates an optical system device and a method that gradually move the region of the interference image 8+31 by sequentially moving the propagation angle of the electron beam. FIG. 5(a) is the same as FIG. 2(a), and illustrates that the electron beam propagates bilaterally on the optical axis and the electron beam is uniformly irradiated to the specimen region and the vacuum region which are disposed symmetrically with the optical axis 2 interposed therebetween, and as a result, the interference image 8+31 by the reference wave region Ref and the observation region 3-1 is prepared. That is, this is a state of the optical system at the time of observing general electron beam interference (electron holography).

FIG. 5(*b*) illustrates a state of the optical system after deflecting the irradiation angle to the specimen 3 by moving a light source 1 above the specimen or an image 11 (crossover) of the light source by an irradiation optical system from the optical axis 2 to a right space in the figure. The specimen 3 and the image 31 of the specimen are not moved by an imaging relationship, even by deflection of the irradiated electron beam, but since the interference region is formed by projection of the central filament electrode 9, the specimen 3 and the image 31 are moved by deflection of the irradiated electron beam. A movement amount thereof is an amount required for the interference image 8+31 by the observation region 3-1 and the observation region 3-2 to be recorded on the image plane 71, and the movement amount depends on the magnification of the optical system illustrated in FIG. 5 or the position (a height on the optical axis) of the electron biprism in the optical system, and is generally approximately submiliradians and a sufficiently adjustable range.

Similarly as the second embodiment, an observation region in a predetermined range is recorded as the interference image by sequentially repeating the work of recording the interference image by the observation region 3-2 and the observation region 3-3 after recording the interference image in the state of FIG. 5(*b*) and by deflecting the electron beam in this direction. With the deflection of the propagation angle of the electron beam, the position on the image plane 71 where the interference image is formed is also moved and the movement is not displayed in FIG. 5, but the movement is compensated by using the magnifying lens system below the objective lens 5 and the deflection system in the magnifying lens system (see FIG. 6).

The method described in the fourth embodiment may be implemented by only a deflection action to an electromagnetic electron beam without mechanical movement of devices. As a result, a mechanical stable state is easily acquired and it is advantageous in improvement of resolution in this method. However, in the double electron biprism interferometer (Patent Document 1), since the interference region coincides with the specimen position, it is difficult to implement the fourth embodiment.

In the method described in the fourth embodiment, manipulation of the optical system is accompanied during a series of interference image recording works, but since a deflection manipulation is main and the magnification is not changed, when the optical conditions such as the interference region width, the interference pattern interval, the observation and recording magnification, and the like are first set, readjustment of the optical system is not required during the work in a range in which a deflection angle is within a range approximate to a near axis. According to the above configuration, since the magnification, and the like are recorded under the same condition, a wide range of phase distribution images may be acquired by performing image arrangement as it is after operating a regeneration image or integrating the phase distributions.

Figure 6:
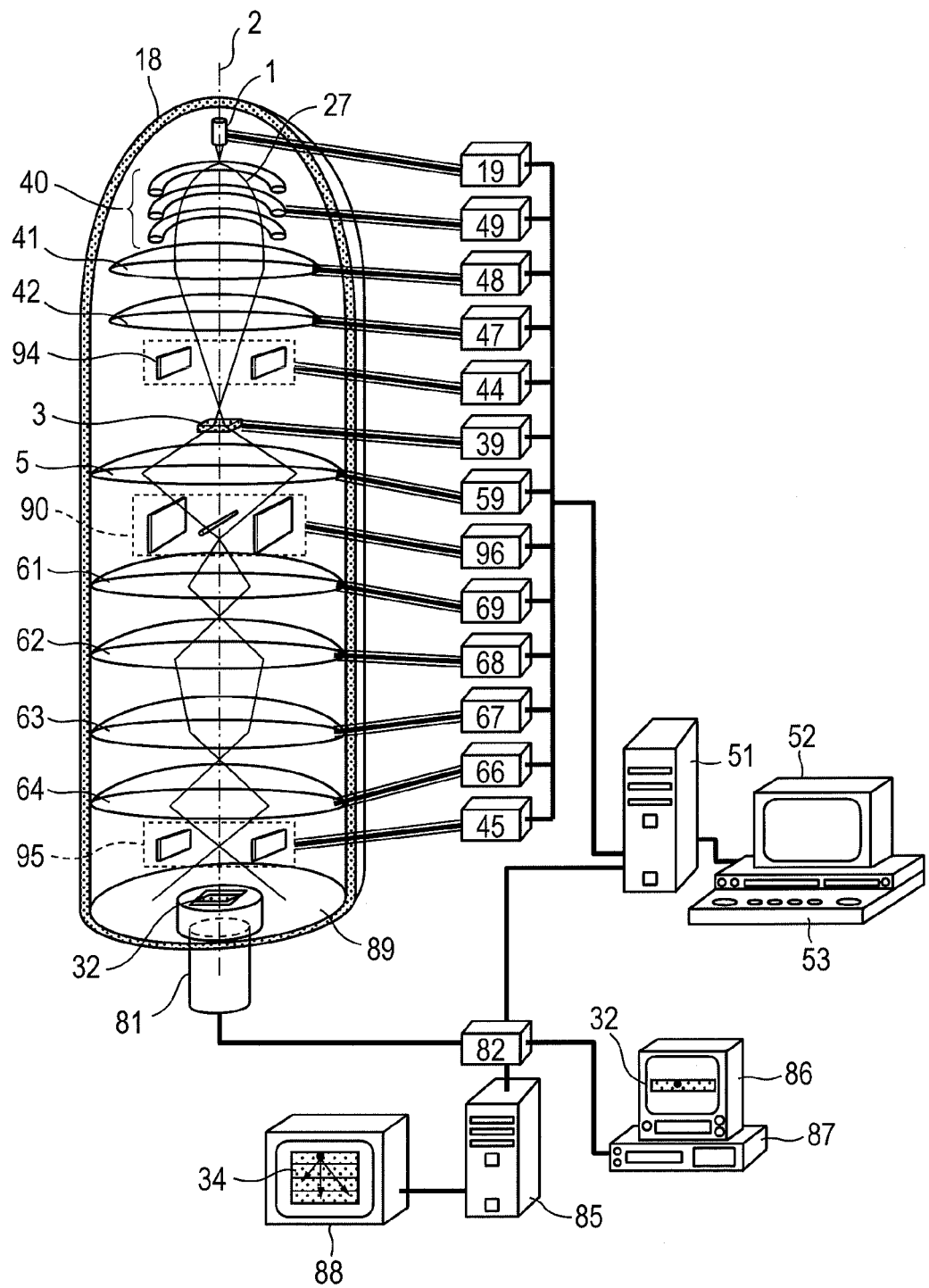
FIG. 6 is a mimetic diagram illustrating an example of a device performing the present invention.

Further, in the fourth embodiment described by using FIG. 5, an example in which the irradiation angle of the electron beam to the specimen is deflected is described, but the present invention is not limited thereto and the figure is omitted, but for example, the deflection system is inserted into the lower part of the objective lens 5 to defect the propagation angle of the electron beam (see FIG. 6). In this case, since a change in an irradiation condition to the specimen is not accompanied, this method is further and further suitable for high resolution than the above method.

Fifth Embodiment

The optical systems illustrated in FIGS. 2, 4, and 5 and an example of an electron beam interference device that may implement the method of FIG. 1 are illustrated in FIG. 6. That is, the electron beam interference device is an electron beam interference device that has an electron biprism 90 disposed below the objective lens 5, and magnifies and observes the interference image acquired on the image plane of the objective lens with magnifying lens systems 61, 62, 63, and 64 constituted by four stages at a rear stage of the objective lens. An interference image 32 imaged on an observation recording plane 89 is recorded by an image observation recording medium 81 (for example, a TV camera or a CCD camera), and regeneration processing of the phase distribution image or integration processing of the phase distribution image are performed by using, for example, an image processing device 85, and the like and an operation result (arranged phase distribution images) 34 is displayed by using a display device 88, and the like.

In implementing this application, the interference image acquired by sequentially moving the observation regions needs to be prepared and recorded, and as a result, the interference image 32 imaged on the observation recording plane 89 is recorded by the image observation recording medium 81 (for example, the TV camera or the CCD camera), and the interference region width acquired at this time is analyzed by a control computer 51 to acquire a value which has already been known. In addition, when the position of the specimen is moved as illustrated in the second embodiment, a micromotion of the specimen position is performed through a specimen control device 39, when the position of the electron biprism is moved as illustrated in the third embodiment, a micromotion of the electron biprism is performed through an electron biprism control device 96, and when the irradiation angle of the electron beam is deflected as illustrated in the fourth embodiment, for example, a deflection device 94 above the specimen is a device that deflects the electron beam through a control device 44 of the deflection system. A deflection device 95 below a magnifying lens 64 is used to adjust the position of the interference image to an appropriate position of the observation recording medium 81. When one micromotion control mechanism that prepares and records the interference image acquired by moving the observation region associated with this application is installed, an object may be achieved, but a state in which the micromotion control mechanisms are arranged in parallel is not excluded.

Further, FIG. 6 illustrates the electron biprism 90 or lenses 61, 62, 63, and 64 of the magnifying imaging system by assuming electron microscopes of 100 kV to 300 kV in the related art, and components of the electron microscope optical system are not limited to components in this figure. In addition, in an actual device, a deflection system that changes a progress direction of the electron beam, an aperture mechanism that limits a transmission region of the electron beam, and the like are present in addition to the components illustrated in FIG. 6. However, devices other than the illustrated devices are not directly associated with the present invention and thus are not illustrated in the figure. Furthermore, the electron optical system is assembled to a vacuum vessel 18 and is continuously exhausted by a vacuum pump and a vacuum exhaust system is not directly associated with the present invention and thus is not illustrated. Even in figures below, the omission will be made similarly.

Sixth Embodiment

The integration processing of the phase distribution images in this application and a meaning thereof have been described by using FIG. 1, and Equations 10 to 15 in the first embodiment. The basis of thinking is in that any one recorded wavefront (for example, a left wavefront in FIG. 2) becomes the other wavefront (for example, a right wavefront in FIG. 2) at the time of recording a subsequent interference image to be offset in integration processing after the regenerated phase distribution is acquired as a differential, in recording the interference image in two-wave interference. In order to appropriately achieve the offset, when two left and right wavefronts interfere with each other, it is important to spatially match the interference regions. A condition therefor indicates a case in which a projection width df of the central filament electrode of the electron biprism onto the specimen plane is small and the width df may be disregarded. Therefore, hereinafter, in a case in which the projection width df of the central filament electrode onto the specimen plane may not be disregarded, a method for more appropriately showing an effect of the present invention will be described.

First, prior to describing the case in which the projection width df of the central filament electrode onto the specimen plane may not be disregarded, the integration processing of the regenerated phase distribution images and replacement of a procedure of arrangement of the respective regenerated phase distribution images will be described by using FIG. 7. FIG. 7 illustrates two wavefronts in two-wave interference. The wavefronts which interfere with each other are divided vertically (in a vertical direction) and arrangement according to the position of the specimen is illustrated horizontally (in a horizontal direction). FIG. 7(a) illustrates a case in which the size of the central filament electrode of the electron biprism may be disregarded. That is, for example, the observation region 3-2 at the time of performing measurement with the observation region 3-2 as the left wavefront and the observation region 3-1 as the right wavefront is the same wavefront as the observation region 3-2 at the time of performing measurement with the observation region 3-3 as the left wavefront and the observation region 3-2 as the right wavefront.

Further, by arranging the adjacent observation regions spatially horizontally, the relationship is continuously implemented to a left side of the specimen in the figure from the reference wave region Ref. This state corresponds to the description using FIG. 1, and Equations 10 to 15. In this case, a relationship of coherence length R>W+df is satisfied.

Next, a wavefront function (phase distribution function) in interference illustrated in FIG. 7(a) is expressed as a 1-dimensional continuous function. When an X axis is set to face a left side, and a boundary between the reference wave region Ref and the observation region 3-1 is set as x=0 which is an original point of a coordinate axis, a left wavefront function is expressed as ηleft(x) and a right wavefront function is expressed as ηright(x−W) by setting the interference region width, that is, a length, in which the wavefront function is spatially moved, as W. Accordingly, a phase distribution function $\Delta\eta(x)$ of the differential is expressed by Equation 16. This is a phase distribution of all of the observation regions acquired by one-time regeneration processing.

$$\Delta\eta(x) = \eta_{left}(x) - \eta_{right}(x-W) \quad \text{[Equation 16]}$$

Herein, when a phase distribution function $\Delta\eta(x-W)$ acquired by moving a variable of the phase distribution function $\Delta\eta(x)$ of the differential by −W is expressed by Equation 17.

$$\Delta\eta(x-W) = \eta_{left}(x-W) - \eta_{right}(x-2W). \quad \text{[Equation 17]}$$

When Equations 16 and 17 are integrated, Equation 18 is acquired.

$$\Delta\eta(x) + \Delta\eta(x-W) = \eta_{left}(x) - \eta_{right}(x-2W) \quad \text{[Equation 18]}$$

This indicates interference of the observation region with a region which is spaced apart by one region. When this is repeated n times until one phase distribution reaches the phase distribution of the reference wave region, this is expressed as Equation 19.

[Equation 19]

$$\sum_{k=1}^{n} \Delta\eta(x-kW) = \eta_{left}(x) - \eta_{right1}(x-kW) = \eta_{left}(x) - \eta_{ref}(x) = \eta_{left}(x)$$

That is, after the respective regenerated phase distributions are arranged as primary regenerated phase distributions in the order of the observation regions, when the phase distributions moved for the width W of the interference region are integrated as many as the number of times according to the order of the respective observation regions, the phase distribution image which extends widely may be acquired. That is, the sixth embodiment is different from the first embodiment in terms of the integration processing and the order of the arrangement work of the regenerated phase distribution images. However, the sixth embodiment is the same as the first embodiment in terms of an acquired result.

Figure 7B:
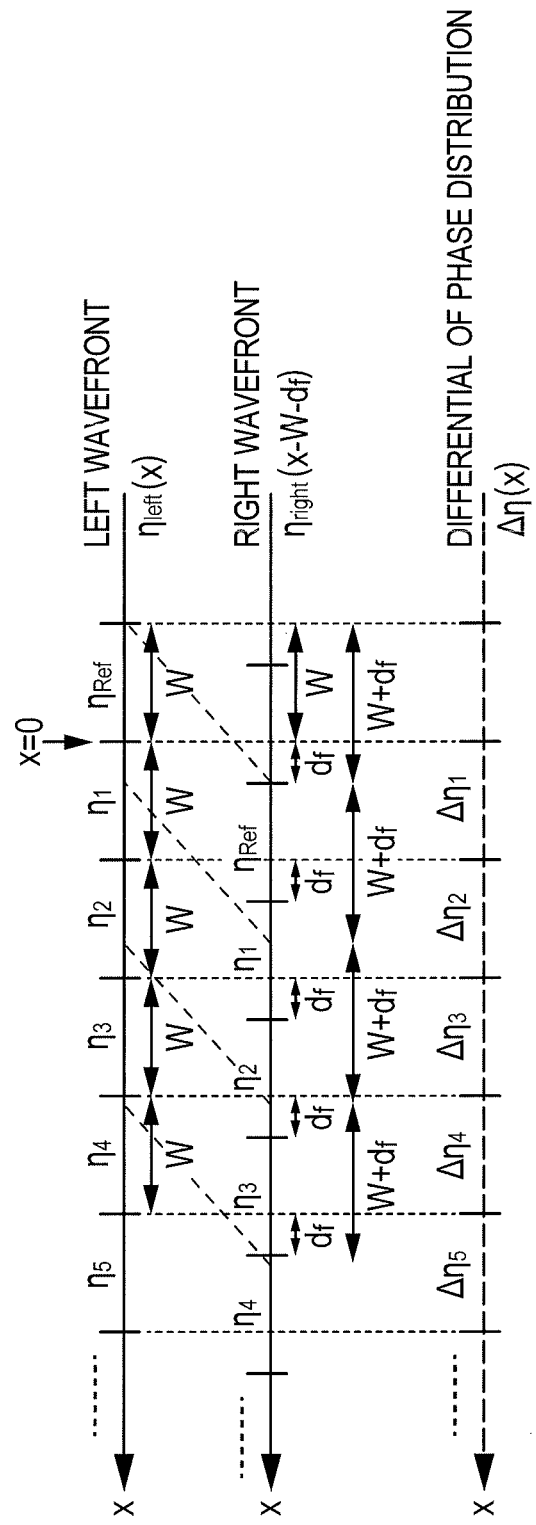
FIG. 7(b) is a mimetic diagram illustrating a spatial positional relationship at the time of subtraction of phase distributions (wavefronts) when the projection width df of the central filament electrode is regarded.

Next, an extension of the case in which the projection width df of the central filament electrode onto the specimen plane may not be disregarded will be described. FIG. 7(b) illustrates two wavefronts in two-wave interference in the case in which the size of the central filament electrode of the electron biprism may not be disregarded. FIG. 7(b) is the same as FIG. 7(a) in terms of the relationship between upper and lower wavefronts, but the relationship between the upper and lower wavefronts indicates that the position of the wavefront displayed on a lower side is moved by the projection width df of the central filament electrode. Although the adjacent observation regions are arranged, the deviation is not resolved, but the deviation is continued throughout an entire region of the wavefront. When the relationship between the wavefronts is expressed by an equation by setting the X axis to face the left side, and the boundary between the reference wave region Ref and the observation region 3-1 as x=0 which is the original point of the coordinate axis, similarly as FIG. 7(a), the left wavefront distribution function is ηleft(x) and the right wavefront function (phase distribution function) is ηright(x−W−df). The phase distribution function $\Delta\eta(x)$ of the differential is expressed by Equation 20.

$$\Delta\eta(x) = \eta_{left}(x) - \eta_{right}(x-W-d_f) \quad \text{[Equation 20]}$$

Herein, similarly as above, when a phase distribution function $\Delta\eta(x-W-df)$ acquired by moving a variable of the phase distribution function $\Delta\eta(x)$ of the differential by −W−df is expressed by Equation 21.

$$\Delta\eta(x-W-d_f) = \eta_{left}(x-W-d_f) - \eta_{right}(x-2(W+d_f)). \quad \text{[Equation 21]}$$

It can be seen that the same handling as Equation 19 is possible by using not the interference region width W but W+df considering the projection width df of the central filament electrode as one unit. This is expressed by Equation 22.

[Equation 22]

$$\sum_{k=1}^{n} \Delta\eta(x - k(W + d_f)) =$$
$$\eta_{left}(x) - \eta_{right1}(x - k(W + d_f)) = \eta_{left}(x) - \eta_{ref}(x) = \eta_{left}(x)$$

That is, after the respective regenerated phase distributions are arranged as primary regenerated phase distributions in the order of the observation regions, when the phase distributions (compensated phase distributions) moved for W+df are integrated as many as the number of times according to the order of the respective observation regions by considering the projection width df of the central filament electrode, the phase distribution image which extends widely may be acquired. That is, the sixth embodiment is different from the first embodiment in terms of the integration processing and the order of the arrangement work of the regenerated phase distribution images. However, as a result, both embodiments are the same as each other in that the regenerated phase distribution image is acquired.

Further, the primary regenerated phase distribution acquired at this time becomes a differential of the phase distributions of regions which are adjacent to each other with the central filament electrode interposed therebetween, and as a result, a wide field phase distribution image in which the phase distributions are arranged becomes an image in which the phase distribution shows a spatial change. For example, when the magnetic line distribution illustrated in FIG. 3($b$) is described, a neighboring part of the MFM tip displays a magnetic line distribution other than a mean magnetic line distribution.

As a result, the method illustrated in the first embodiment and FIG. 1 or FIG. 7($a$) corresponds to a case in which the projection width df of the central filament electrode is zero. Accordingly, when the projection width df of the central filament electrode is small to be disregarded as compared with the interference region or the phase distribution is not rapidly changed within the range of the width df because the change in phase distribution is gentle, the phase distribution may be approximately regenerated by the method illustrated in the first embodiment, and FIG. 1 or FIG. 7($a$).

Seventh Embodiment

In regard to handling when the projection width df of the central filament electrode onto the specimen plane may not be disregarded, a separate method from the sixth embodiment will be described based on FIG. 8.

Figure 8:
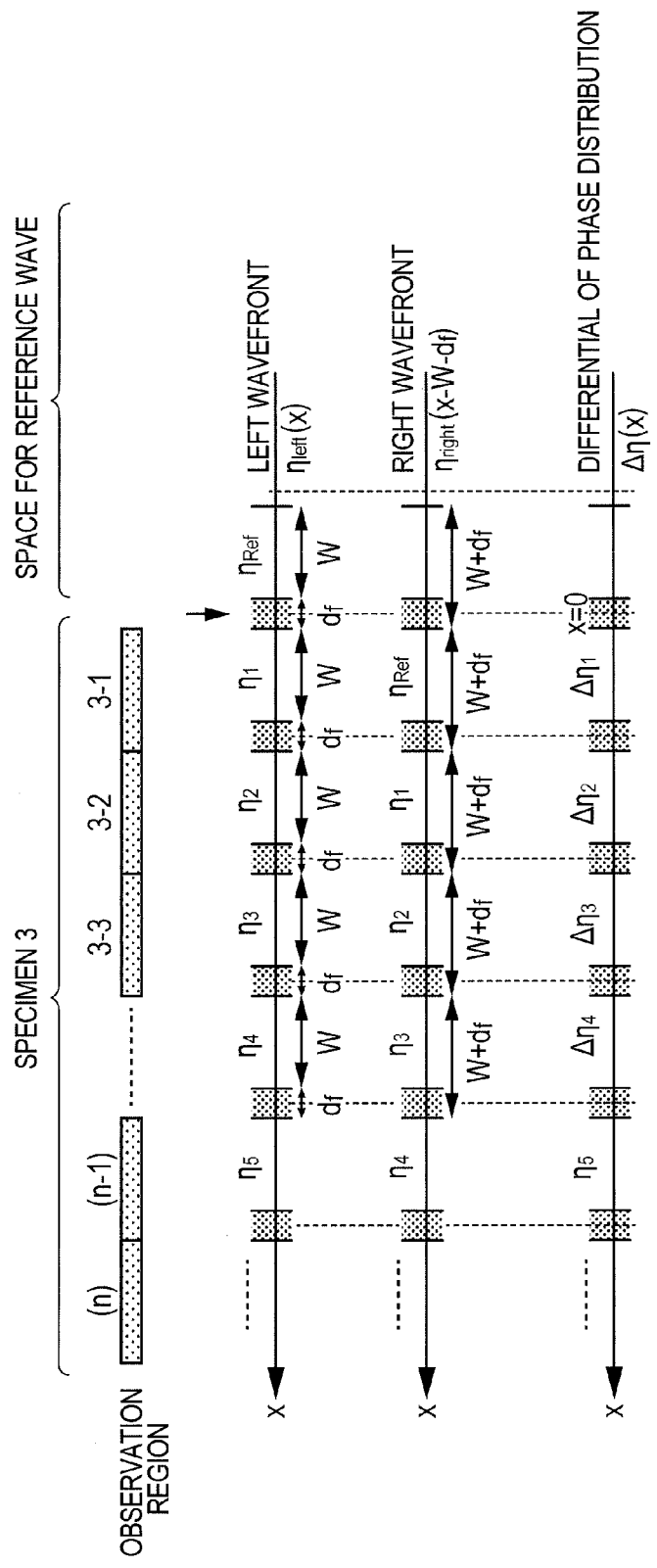
FIG. 8 is a mimetic diagram describing a case of moving by summing up an interference region width W and the projection width df of the central filament electrode.
Figure 11:
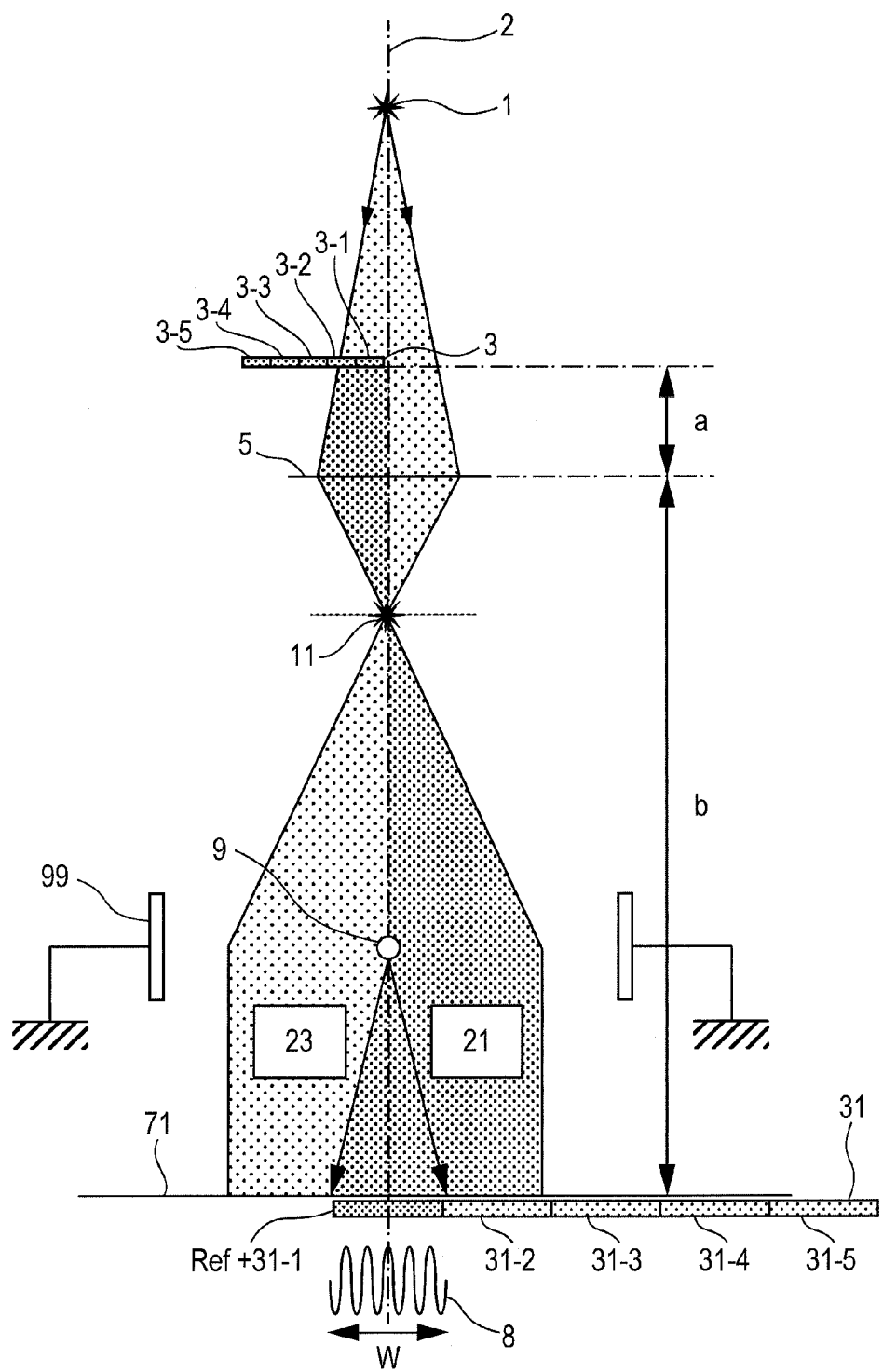
FIG. 11 is a mimetic diagram of an optical system describing an electron beam interferometry.

FIG. 8 illustrates a state in which the interference image is prepared by moving by W+df by adding not the interference region width W but the projection width df of the central filament electrode at the time of preparing the interference image of the adjacent observation regions. By this method, a condition is satisfied, in which any one recorded wavefront (for example, the left wavefront in FIG. 11) needs to become the other wavefront (for example, the right wavefront in FIG. 11) at the time of recording a subsequent interference image. However, a defective region of information is generated between the respective wavefronts acquired from the respective interference images as large as the projection width df of the central filament electrode. Regeneration precision deteriorates as compared with the sixth embodiment, but this method is effective when a burden for image processing after an experiment is small, the projection width df of the central filament electrode is small no to influence all image information as compared with the interference region width W or the phase distribution is not rapidly changed within the range of the width df because the change in phase distribution is gentle. Even in this case, the relationship of coherence length R>W+df needs to be satisfied.

Eighth Embodiment

Similarly as the seventh embodiment, a separate method regarding handling when the projection width df of the central filament electrode onto the specimen plane may not be disregarded will be described based on FIG. 9.

Figure 9:
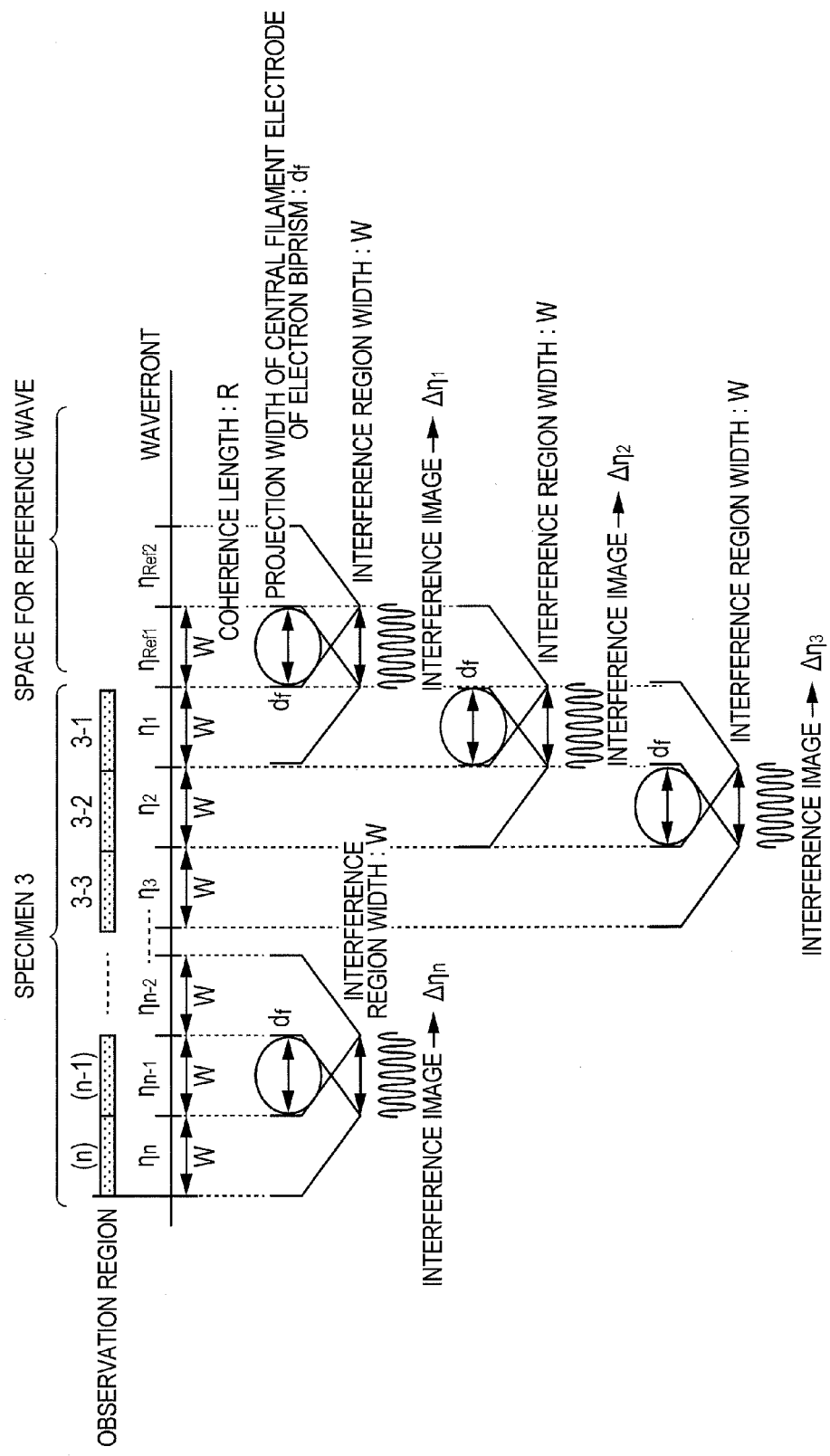
FIG. 9 is a mimetic diagram describing a method of preparing consecutive interference images for each of adjacent regions when the interference region width W and the projection width df of the central filament electrode coincide with each other.
Figure 10:
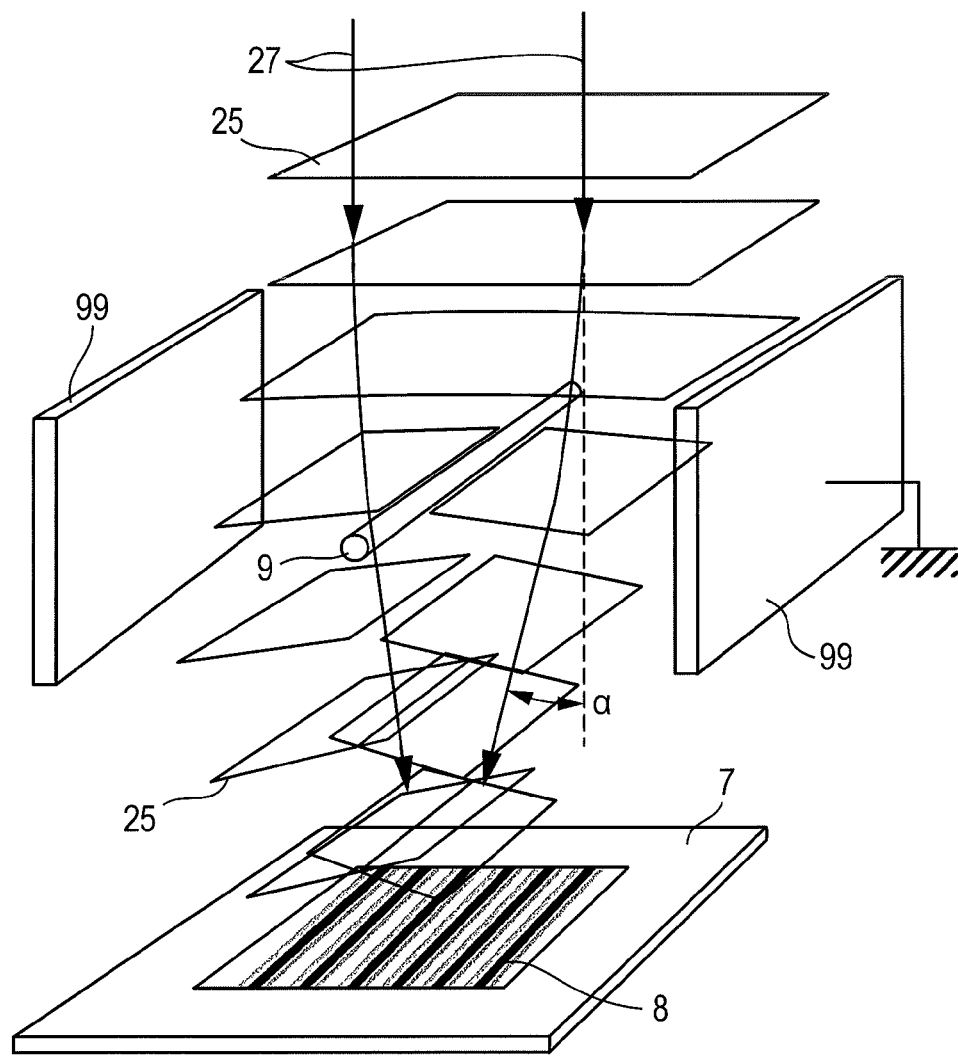
FIG. 10 is a mimetic diagram describing a relationship among an electric field type electron biprism, a trajectory of an electron beam, and a wavefront.

FIG. 9 illustrates a state in which the interference image is prepared by moving the observation regions every the interference region width W similarly as the first embodiment after adjusting application voltage to the central filament electrode so that the projection width df of the central filament electrode and the interference region width W coincide with each other, at the time of preparing the interference image of adjacent observation regions. As apparently known from FIG. 9, according this method, the condition is satisfied, in which any one recorded wavefront (for example, the left wavefront in FIG. 11) needs to become the other wavefront (for example, the right wavefront in FIG. 11) at the time of recording another interference image between phase distributions from any observation region and a region separated by one region (for example, the observation region 3-1 and the observation region 3-3).

That is, handling becomes possible for each odd region and for each even region, similarly as the first embodiment. However, two regions are required as the reference wave region, but in a general interference experiment, this is not problematic. Just to be safe, hereinafter, equations regarding the phase distribution images of the respective differentials and phase distribution images based on reference waves acquired by integration thereof are enumerated with respect to the observation regions 3 to 5. This method is a practicable method in which the burden for the image processing after the experiment is small. A condition which needs to be satisfied in this case is coherence length R>2W.

$\Delta\eta_1(x,y)=\eta_1(x,y)-\eta_{Ref2}(x,y)$ [Equation 23]

$\Delta\eta_2(x,y)=\eta_2(x,y)-\eta_{Ref1}(x,y)$ [Equation 24]

$\Delta\eta_3(x,y)=\eta_3(x,y)-\eta_1(x,y)$ [Equation 25]

$\Delta\eta_4(x,y)=\eta_4(x,y)-\eta_2(x,y)$ [Equation 26]

$\Delta\eta_5(x,y)=\eta_5(x,y)-\eta_3(x,y)$ [Equation 27]

$\eta_{Ref1}(x,y)=\eta_{Ref2}(x,y)$ [Equation 28]

$\Delta\eta_5(x,y)+\Delta\eta_3(x,y)+\Delta\eta_1(x,y)=\eta_5(x,y)-\eta_{Ref2}(x,y)=\eta_5(x,y)$ [Equation 29]

Further, although a case in which the projection width df of the central filament electrode and the interference region width W coincide with each other has been described in the embodiment, when the projection width df of the central filament electrode is integer times (N times) larger than the interference region width W, the number of regions skipped among the recorded regions is just increased and the number may be easily extended as the same handling. A condition which needs to be satisfied in this case is coherence length R>NW.

Ninth Embodiment

In an electron beam interference experiment using a CCD camera, an interference image between reference waves spaced apart from an observation target is recorded as a reference hologram other than a hologram which is the objection target, and a phase distribution image regenerated from a reference hologram is subtracted from the phase distribution image regenerated from the hologram which is the observation target to frequently perform, for example, operation processing to offset an influence of charge-up generated in the central filament electrode of the electron biprism (Non-Patent Document 2). This application is not contrary to the method in the related art, but is a completely compatible method. This method will be described by using equations.

A phase distribution caused by the charge-up generated in the central filament electrode of the electron biprism is represented by ηch. This is a phase distribution which is continuously and similarly generated when the interference image is recorded and regenerated without depending on the object wave and the reference wave. Strictly, whether the differential is a subtracted term or a subtracting term of the phase distribution depends on whether a generation position of the charge-up on the central filament electrode is an object wave side or a reference wave side, but as a result, since only a distribution after the differential is detected, the phase distribution after the differential is ηch. Therefore, for example, phase distributions of an n-th observation region n and an n-1-th observation region n-1 are expressed by Equation 30 and the phase distribution of the reference hologram is expressed by Equation 31.

$$\Delta\eta_n(x,y)=\eta_n(x,y)-\eta_{n-1}(x,y)+\eta_{ch}(x,y) \quad [\text{Equation 30}]$$

$$\Delta\eta_{RefHolo}(x,y)=\eta_{ch}(x,y) \quad [\text{Equation 31}]$$

Herein, when subtraction of Equation 31 from Equation 30 is performed again, Equation 32 is acquired.

$$\Delta\eta'_n(x,y)=\eta_n(x,y)-\eta_{RefHolo}(x,y)=\eta_n(x,y)-\eta_{n-1}(x,y) \quad [\text{Equation 32}]$$

Equation 32 is the same as Equation 14 in this viewpoint. That is, when Δηn of Equation 13 is acquired by modifying Δη'n of Equation 32, it can be seen that all of the methods of this application which have been described up to now may be implemented. Further, the experimental example illustrated in FIG. 3 is performed by using the reference hologram.

That is, in this application, as long as interference of electron waves that is transmitted through the specimen is recorded, a predetermined part in the specimen may be holograph-observed by integrating phase distribution images regenerated from the interference image. As a result, the electron beam interferometry is released from a condition which is a most important and principle limitation of the electron beam interferometry in the related art, in which the observation region is limited to a neighboring part of the reference wave.

LIST OF REFERENCE SIGNS 1 electron source or electron gun
11 crossover
18 vacuum vessel
19 control unit of electron source
2 optical axis
21 object wave
23 reference wave
25 wavefront
27 trajectory of electron beam
3 specimen
31 image of specimen imaged by objective lens
32 image of specimen imaged on observation recording system
34 arranged phase distribution images
40 acceleration tube
41 first irradiation lens
42 second irradiation lens
44 control unit of defection device installed in irradiation system
45 control unit of defection device installed in imaging system
47 control unit of second irradiation lens
48 control unit of first irradiation lens
49 control unit of acceleration tube
5 objective lens
51 control system computer
52 monitor of control system monitor
53 interface of control system computer
59 control unit of objective lens
61 first imaging lens
62 second imaging lens
63 third imaging lens
64 fourth imaging lens
66 control unit of fourth imaging lens
67 control unit of third imaging lens
68 control unit of second imaging lens
69 control unit of first imaging lens
7 image plane
71 image plane of specimen by objective lens
8 interference pattern
81 image observation recording medium
82 control unit of image observation recording medium
85 image operation processing device
86 monitor of image operation processing device
87 interface of image operating processing device
88 display device
89 observation recording plane
9 central filament electrode of electron biprism
90 electron biprism
94 deflection device installed in irradiation system
95 deflection device installed in imaging system
99 parallel plate ground electrode
3-1 first observation region
3-2 second observation region
3-3 third observation region
3-4 fourth observation region
3-5 fifth observation region
(n) n-th observation region
(Ref) reference wave region

The invention claimed is:
1. An electron beam interference device, comprising:
a light source of an electron beam;
an irradiation optical system for irradiating an electron beam emitted from the light source to a specimen;
an imaging lens system having an objective lens that images an image of the specimen;
an electron biprism disposed on an optical axis of the electron beam;
an image recording device recording a plurality of phase distribution images in the specimen; and
an image operation processing device operating the phase distribution images of the specimen, wherein the specimen includes a first observation region that an electron beam through which interferes with an electron beam transmitted through a reference wave region by the electron biprism is transmitted and a second observation region that an electron beam which interferes with the electron beam transmitted through the first observation region by the electron biprism is transmitted, the image recording device records a second interference image based on the electron beam transmitted through the first observation region and the electron beam transmitted through the second observation region while recording a first interference image based on the electron beam transmitted through the reference wave region and the electron beam transmitted through the first observation region, and the image operation processing device operates phase distribution images of the electron beam transmitted through the reference wave region and the electron beam transmitted through the second observation region based on the second interference image recorded in the image recording device and the first interference image recorded in the image recording device.

2. The electron beam interference device according to claim 1, wherein the image operation processing device, operates a first phase distribution image from the first interference image based on the electron beam transmitted through the reference wave region and the electron beam transmitted through the first observation region, operates a second phase distribution image from the second interference image based on the electron beam transmitted through the first observation region and the electron beam transmitted through the second observation region, and operates phase distribution images of the electron beam transmitted through the reference wave region and the electron beam transmitted through the second observation region by acquiring the sum of the first phase distribution image and the second phase distribution image.

3. The electron beam interference device according to claim 1, further comprising:

a specimen storing and holding device for holding a specimen to which the electron beam is irradiated, wherein the specimen storing and holding device moves the specimen in a vertical direction to the optical axis and in a vertical direction to a length direction of a projection image of the electron biprism at the time of recording the first interference image and the second interference image.

4. The electron beam interference device according to claim 1, further comprising:

a biprism moving means moving the position of the electron biprism, wherein the biprism moving means moves the electron biprism in the vertical direction to the optical axis at the time of recording the first interference image and the second interference image.

5. The electron beam interference device according to claim 1, wherein the irradiation optical system changes a propagation angle which the electron beam forms with the optical axis at the time of recording the first interference image and the second interference image.

6. The electron beam interference device according to claim 1, further comprising:

an image display device arranging and displaying the operated phase distribution images in the order in which interference images which become origins of the operated phase distribution images are recorded.

7. An electron beam interferometry including, a light source of an electron beam;

an irradiation optical system for irradiating an electron beam emitted from the light source to a specimen;

an imaging lens system having an objective lens that images an image of the specimen;

an electron biprism disposed on an optical axis of the electron beam;

an image recording device recording a plurality of interference images in the specimen; and an image operation processing device operating the phase distribution images of the specimen, the electron beam interferometry comprising:

a first step of recording a first interference image based on a first observation region that an electron beam through which interferes with an electron beam transmitted through a reference wave region by the electron biprism is transmitted and the electron beam transmitted through the reference wave region;

a second step of recording a second interference image based on a first observation region that an electron beam through which interferes with an electron beam transmitted through the second observation region by the electron biprism is transmitted, and the electron beam transmitted through the first observation region; and a third step of operating phase distribution images of the electron beam transmitted through the reference wave region and the electron beam transmitted through the second observation region based on the second interference image and the first interference image.

8. The electron beam interferometry according to claim 7, wherein the third step includes a fourth step of operating first phase distribution images of the electron beam transmitted through the reference wave region and the electron beam transmitted through the first observation region based on the first interference image, a fifth step of operating the second phase distribution image of the electron beam transmitted through the first observation region and the electron beam transmitted through the second observation region based on the second interference image, and a sixth step of operating phase distribution images of the electron beam transmitted through the reference wave region and the electron beam transmitted through the second observation region by summing up the first phase distribution image and the second phase distribution image.

9. The electron beam interferometry according to claim 7, further comprising:

a seventh step of arranging and displaying the operated phase distribution images in the order in which interference images which become origins of the operated phase distribution images are recorded.

10. An electron beam interferometry including, a light source of an electron beam;

an irradiation optical system for irradiating an electron beam emitted from the light source to a specimen;

an imaging lens system having an objective lens that images an image of the specimen;

an electron biprism disposed on an optical axis of the electron beam;

an image recording device recording a plurality of interference images in the specimen; and an image operation processing device operating the phase distribution images of the specimen, the electron beam interferometry comprising:

a first step of recording a first interference image based on a first observation region that an electron beam through which interferes with an electron beam transmitted through a reference wave region by the electron biprism is transmitted and the electron beam transmitted through the reference wave region;

a second step of recording a second interference image based on an electron beam transmitted through a first observation region that an electron beam through which interferes with an electron beam transmitted through the second observation region by the electron biprism is transmitted, and the electron beam transmitted through the first observation region;

a third step of operating first phase distribution images of the electron beam transmitted through the reference wave region and the electron beam transmitted through the first observation region based on the first interference image;

a fourth step of operating second phase distribution images of the electron beam transmitted through the first observation region and the electron beam transmitted through the second observation region based on the second interference image; and a fifth step of arranging and displaying the operated first and second phase distribution images in the order in which interference images which become origins of the operated phase distribution images are recorded.

11. The electron beam interferometry according to claim 10, further comprising:

a sixth step of moving the arranged phase distribution images in a vertical direction to a length direction of a projection image of the electron biprism at a predetermined amount to be first compensated phase distribution images; and a seventh step of operating phase distribution images of the electron beam transmitted through the reference wave region and the electron beam transmitted through the second observation region by summing up the arranged phase distribution images and the first compensated phase distribution images.

12. The electron beam interferometry according to claim 11, wherein the predetermined amount is an interference region width.

13. The electron beam interferometry according to claim 11, wherein the predetermined amount is the sum of the interference region width and a projection width of a central filament electrode of the electron biprism.

14. The electron beam interferometry according to claim 11, wherein the predetermined amount is integer times more than the interference region width.

* * * * *